United States Patent
Zimmermann et al.

(12)

(10) Patent No.: US 6,395,732 B1
(45) Date of Patent: May 28, 2002

(54) PYRIMIDIN-AMINOMETHYL-PYRIDINE DERIVATIVES, THEIR PREPARATION AND THEIR USE IN THE CONTROL OF HELICOBACTER BACTERIA

(75) Inventors: Peter Zimmermann, Allensbach; Gerhard Grundler, Constance, both of (DE)

(73) Assignee: BYK Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/700,681

(22) PCT Filed: May 20, 1999

(86) PCT No.: PCT/EP99/03477

§ 371 (c)(1),
(2), (4) Date: Nov. 17, 2000

(87) PCT Pub. No.: WO99/61439

PCT Pub. Date: Dec. 2, 1999

(30) Foreign Application Priority Data

May 23, 1998 (EP) .............................................. 98109408

(51) Int. Cl.⁷ ........................ A61K 31/54; A61K 31/15; C07D 417/00; C07D 413/00; C07D 253/00
(52) U.S. Cl. ............................... 514/227.8; 514/231.5; 514/241; 514/242; 514/248; 514/252.14; 514/256; 544/60; 544/111; 544/180; 544/182; 544/235; 544/328
(58) Field of Search .......................... 514/227.8, 231.5, 514/241.242, 248, 252.14, 256; 544/60, 111, 180, 182, 235, 328

(56) References Cited

FOREIGN PATENT DOCUMENTS

| EP | 264 883 | 4/1988 |
| WO | WO 96/02505 | 2/1996 |
| WO | WO 97/34873 | 9/1997 |

OTHER PUBLICATIONS

Whitehead, C. et al., "Diuretics. III. 4,6–Diaminopyrimidines" *Jour. Of the American Chem.* Soc., Bd. 80, 5.5.58,pp. 2185–2189 (Oct. 21, 1957).

Patent Abstracts of Japan, vol. 96, No. 5, 31.5.96 & JP 08012671, 1996.

*Primary Examiner*—Richard L. Raymond
*Assistant Examiner*—Tamthom N. Truong
(74) *Attorney, Agent, or Firm*—Nath & Associates PLLC; Gary M. Nath; Todd L. Juneau

(57) ABSTRACT

The present invention relates to compounds of formula (I) wherein R1, R2, and R3 are hydrogen, 1–4C-alkyl, or halogen; R4, R5, R6, and R9 are hydrogen or 1–4C-alkyl; R7 and R8 are hydrogen, 1–4C-alkyl, 1–4C-alkoxy, or halogen; A is 1–7C-alkylene, 2–7C-alkenylene, 3–7C-cycloalkylene, or phenylene; G is hydrogen, hydroxyl, 1–7C-alkyl, 1–4C-alkyl substituted by fluorine, 2–7C-alkenyl, 3–7C-cycloalkyl, a mono- or di-1–4C-alkylcarbamoyl or -thiocarbamoyl, N-1–4C-alkyl-N'-cyanoamidino, 1-N-1–4C-alkylamino-2-nitroethylene, N-2-propynyl-N'-cyanoamidino, aminosulfonylamidino, —N(R10)R11, the part of the compound of formula (I) bonded to A, glucopyranoside, or a cyclic system or bicyclic system which is optionally substituted by R12 and R13; X is oxygen, N-1–4C-alkyl, NH, or S; Y is oxygen, N-1–4C-alkyl, NH, S, 1,4-piperazinylene, or 1,4-piperidinylene; Z is oxygen, N-1–4C-alkyl, NH, S, or CO; m is from 1 to 7; n is from 0 to 4; t is 0, 1, or 2; and u is 0 or 1, and their salts suitable for controlling Helicobacter bacteria.

10 Claims, No Drawings

PYRIMIDIN-AMINOMETHYL-PYRIDINE DERIVATIVES, THEIR PREPARATION AND THEIR USE IN THE CONTROL OF HELICOBACTER BACTERIA

FIELD OF APPLICATION OF THE INVENTION

The invention relates to compounds which are intended to be used in the pharmaceutical industry as active compounds for the production of medicaments.

PRIOR ART

International Patent Applications WO 94/13290, 94/19346, 95/01351, 95/15324, 96/00224, 95/34554, 95/34553, 96/02534 and 96/02505 describe benzimidazole and imidazopyridine derivatives which are said to be suitable for the control of Helicobacter bacteria.

DESCRIPTION OF THE INVENTION

The invention relates to compounds of the formula I in which

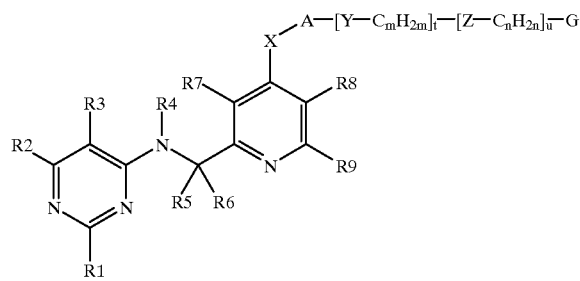

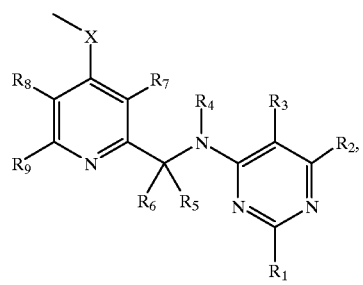

R1, R2 and R3 are identical to or different from one another and are hydrogen, 1–4C-alkyl or halogen, R4 is hydrogen or 1–4C-alkyl, R5 is hydrogen or 1–4C-alkyl, R6 is hydrogen or 1–4C-alkyl, R7 is hydrogen, 1–4C-alkyl, 1–4C-alkoxy or halogen, R8 is hydrogen, 1–4C-alkyl, 1–4C-alkoxy or halogen, R9 is hydrogen or 1–4C-alkyl, A is 1–7C-alkylene, 2–7C-alkenylene, 3–7C-cycloalkylene or phenylene, G is hydrogen, hydroxyl, 1–7C-alkyl, 1–4C-alkyl which is completely or mainly substituted by fluorine, 2–7C-alkenyl, 3–7C-cycloalkyl, a mono- or di-1–4C-alkylcarbamoyl or -thiocarbamoyl radical, an N-1–4C-alkyl-N'-cyanoamidino radical, a 1-N-1–4C-alkylamino-2-nitroethylene radical, an N-2-propynyl-N'-cyanoamidino radical, an aminosulfonylamidino radical, the radical -N(R10)R11, the glucopyranoside radical or a cyclic system or bicyclic system which is unsubstituted or substituted by R12 and R13 and which is selected from the group consisting of benzene, naphthalene, furan, thiophene, pyrrole, oxazole, oxazoline, oxazolidinone, isoxazole, thiazole, thiazoline, isothiazole, imidazole, imidazoline, pyrazole, triazole, tetrazole, thiadiazole, thiodiazole 1-oxide, oxadiazole, pyridine, pyridine N-oxide, pyrimidine, halopyrimidine, piperidine, triazine, pyridone, benzimidazole, imidazopyridine, benzothiazole, benzoxazole, quinoline and imidazopyridazine, in which R10 is 1–7C-alkyl, 3–7C-cycloalkyl or Ar-1–4C-alkyl and R11 is 1–7C-alkyl, 3–7C-cycloalkyl or Ar-1–4C-alkyl, where Ar is phenyl, furyl, naphthyl, tetrahydronaphthyl or phenyl which is substituted by R14, R15 and R16, or in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, thiomorpholine, indoline, 1,2,3,4-tetrahydroquinoline and 1,2,3,4-tetrahydroisoquinoline, where a substituted pyrrolidino radical is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl, a substituted piperidino radical is substituted by one, two or three identical or different substituents selected from the group consisting of 1–4C-alkyl, 1–4C-alkoxycarbonyl, hydroxy-1–4C-alkyl, phenyl or phenyl-1–4C-alkyl, which is substituted by R14, R15 and R16, benzoyl, benzoyl substituted by halogen and carboxyl, a substituted piperazino radical can be substituted in the 2-, 3-, 5- or 6-position by a 1–4C-alkyl radical, and is substituted in the 4-position by a substituent selected from the group consisting of 1–4C-alkyl, 3–7C-cycloalkyl, 3–7C-cycloalkyl-1–4C-alkyl, 1–4C-alkoxy-carbonyl-1–4C-alkyl and carbamoyl, a substituted morpholino radical is substituted by one or two identical or different 1–4C-alkyl radicals, a substituted thiomorpholino radical is substituted by one or two identical or different 1–4C-alkyl radicals or a carboxyl group, a substituted indolin-1-yl radical can be substituted in the 2- and/or 3-position by a carboxyl group or by one or two identical or different 1–4C-alkyl radicals, and can be substituted in the benzo moiety by one or two identical or different substituents selected from the group consisting of 1–4-alkyl, halogen and nitro, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical is substituted by one or two identical or different substituents selected from the group consisting of 1–4C-alkyl, carboxyl and phenyl, R12 is hydrogen, 1–4C-alkyl, hydroxyl, 1–4C-alkoxy, halogen, nitro, guanidino, carboxyl, 1–4C-alkoxycarbonyl, 1–4C-alkyl substituted by R17, phenyl substituted by R14, R15 and R16 or —N(R18)R19, R13 is hydrogen, 1–4C-alkyl, hydroxyl, 1–4C-alkoxy, halogen or trifluoromethyl, R14 is hydrogen, 1–4C-alkyl, hydroxyl, 1–4C-alkoxy, 1–4C -alkylcarbonyl, halogen, trifluoromethyl, 1–4C-alkylamino or nitro, R15 is hydrogen, 1–4C-alkyl, hydroxyl, 1–4C-alkoxy, halogen or nitro, and R16 is hydrogen or trifluoromethyl, R17 is hydroxyl, 1–4C-alkoxy, carboxyl, 1–4C-alkoxycarbonyl, pyridinyl or —N(R18)R19, where R18 is hydrogen, 1–4C-alkyl or —CO—R20 and R19 is hydrogen or 1–4C-alkyl, or where R18 and R19, together and including the nitrogen atom to which both are bonded, are a piperidino or morpholino radical, R20 is hydrogen, 1–4C-alkyl or 1–4C-alkoxy, X is O (oxygen), N-1–4C-alkyl, NH or S, Y is O (oxygen), N-1–4C-alkyl, NH, S, 1,4-piperazinylene or 1,4-piperidinylene, Z is O (oxygen), N—4C-alkyl, NH or S or CO, m is a number from 1 to 7, n is a number from 0 to 4, t is the number 0, 1 or 2 and u is the number 0 or 1, and their salts.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1–4C-Alkoxy represents a radical which, in addition to the oxygen atom, contains one of the abovementioned 1–4C-alkyl radicals. Examples which may be mentioned are the methoxy and the ethoxy radicals.

Halogen within the meaning of the present invention is bromine, chlorine or fluorine.

1–7C-Alkylene represents straight-chain or branched 1–7C-alkylene radicals, for example the methylene (—CH$_2$—), ethylene (—CH$_2$—CH$_2$—), trimethylene (—CH$_2$—CH$_2$—CH$_2$—), tetramethylene (—CH$_2$—CH$_2$—CH$_2$—CH$_2$—), 1,2-dimethylethylene [—CH(CH$_3$)—CH(CH$_3$)—], 1,1-dimethylethylene [—C(CH$_3$)$_2$—CH$_2$—], 2,2-dimethylethylene [—CH$_2$—C(C$_3$)$_2$—], isopropylidene [—C(CH$_3$)$_2$—], 1-methylethylene [—CH(CH$_3$)—CH$_2$—], pentamethylene (—CH$_2$—CH$_2$—CH$_2$—CH$_2$—CH$_2$—), hexamethylene (—CH$_2$—CH$_2$—CH$_2$—CH$_2$—CH$_2$—CH$_2$—) and the heptamethylene (—CH$_2$—CH$_2$—CH$_2$—CH$_2$—CH$_2$—CH$_2$—CH$_2$—) radicals. When t is the number 1 or t is the number 0 and at the same time u is the number 1, A preferably has the meaning 2–7C-alkylene. Of the alkylene radicals A, the ethylene, the propylene and the butylene radicals are preferred.

2–7C-Alkenylene represents straight-chain or branched 2–7C-alkenylene radicals, under which is understood a mono- or polyunsaturated divalent hydrocarbon radical. Examples which may be mentioned are the vinylene (—CH═CH—), 1-propenylene (—CH═CH—CH$_2$—), 2-butenylene (—CH$_2$—CH═CH—CH$_2$—) and the 1,3-butadienylene (—CH═CH—CH═CH—) radicals.

3–7C-Cycloalkyl represents cyclopropyl, cyclobutyl, cyclopentyl, cyclohexyl and cycloheptyl.

3–7C-Cycloalkylene represents one of the abovementioned 3–7C-cycloalkyl radicals having two bonds. An example which may be mentioned is the 1,4-cyclohexylene radical.

Phenylene represents the 1,2-, 1,3- and 1,4-phenylene radicals, of which the 1,4-phenylene radical is preferred.

1–7C-Alkyl represents straight-chain or branched alkyl radicals having 1 to 7 carbon atoms. Examples which may be mentioned are the heptyl, isoheptyl, (5-methylhexyl), hexyl, isohexyl (4-methylpentyl), neohexyl (3,3-dimethylbutyl), pentyl, isopentyl-(3-methylbutyl), neopentyl (2,2-dimethylpropyl), butyl, iso-butyl, sec-butyl, tert-butyl, propyl, isopropyl, ethyl and methyl radicals.

Examples of 1–4C-alkyl which is completely or mainly substituted by fluorine are the 2,2,3,3,3-pentafluoropropyl, the perfluoroethyl and the 1,2,2-trifluoroethyl radicals, in particular the 1,1,2,2-tetrafluoroethyl, the 2,2,2-trifluoroethyl, the trifluoromethyl and the difluoromethyl radicals.

2–7C-Alkenyl represents straight-chain or branched alkenyl radicals having 2 to 7 carbon atoms. Examples which may be mentioned are the 2-butenyl, 3-butenyl, 1-propenyl, 2-propenyl (allyl) and vinyl radicals.

Mono- or di-1–4C-alkylcarbamoyl radicals are carbamoyl radicals (—CO—NH$_2$) which are substituted by one or two identical or different 1–4C-alkyl radicals from those mentioned above. Examples which may be mentioned are the methylcarbamoyl, the isopropylcarbamoyl and the dimethylcarbamoyl radicals.

Mono- or di-1–4C-alkylthiocarbamoyl radicals are thiocarbamoyl radicals (—CS—NH$_2$) which are substituted by one or two identical or different 1–4C-alkyl radicals from those mentioned above. Examples which may be mentioned are the methylthiocarbamoyl, the isopropylthiocarbamoyl and the dimethylthiocarbamoyl radicals.

An example of an N-1–4C-alkyl-N'-cyanoamidino radical which may be mentioned is in particular the N-methyl-N'-cyanoamidino radical [—C(═NCN)—NH—CH$_3$].

An example of a 1-N-1–4C-alkylamino-2-nitroethylene radical which may be mentioned is in particular the 1-N-methylamino-2-nitroethylene radical [—C(NHCH$_3$)═CHNO$_2$].

Exemplary radicals —[Z—C$_n$H$_{2n}$]$_u$—G where G=an N-1–4C-alkyl-N'-cyanoamidino radical, 1-N-1–4C-alkylamino-2-nitroethyl radical or N-2-propynyl-N'-cyanoamidino radical to be mentioned are in particular those radicals in which Z has the meaning NH and n is the number 0. In this connection, radicals —[Z—C$_n$H$_{2n}$]$_u$—G particularly to be mentioned are the radicals —NH—C(═NCN)NH—CH$_3$, —NH—C(NHCH$_3$)═CHNO$_2$ and —NH—C(═NCN)NH—CH$_2$C≡CH.

1–4C-Alkoxy-1–4C-alkyl represents one of the abovementioned 1–4C-alkyl radicals which is substituted by one of the abovementioned 1–4C-alkoxy radicals. Examples which may be mentioned are the methoxymethyl radical, the methoxyethyl radical and the butoxyethyl radical.

1–4C-Alkoxycarbonyl represents a carbonyl group to which one of the abovementioned 1–4C-alkoxy radicals is bonded. Examples which may be mentioned are the methoxycarbonyl ($CH_3O$—C(O)—) and the ethoxycarbonyl ($CH_3CH_2O$—C(O)—) radicals.

In addition to the oxygen atom, 1–4C-alkoxycarbonyloxy radicals contain one of the abovementioned 1–4C-alkylcarbonyl radicals. An example which may be mentioned is the acetoxy radical ($CH_3CO$—O—).

Hydroxy-1–4C-alkyl represents abovementioned 1–4C-alkyl radicals which are substituted by a hydroxyl group. Examples which may be mentioned are the hydroxymethyl, the 2-hydroxyethyl and the 3-hydroxypropyl radicals.

3–7C-Cycloalkyl-1–4C-alkyl represents one of the abovementioned 1–4C-alkyl radicals which is substituted by one of the abovementioned 3–7C-cycloalkyl radicals. Examples which may be mentioned are the cyclopropylmethyl, the cyclohexylmethyl and the cyclohexylethyl radicals.

1–4C-Alkoxycarbonyl-1–4C-alkyl represents one of the abovementioned 1–4C-alkyl radicals which is substituted by one of the abovementioned 1–4C-alkoxycarbonyl radicals. An example which may be mentioned is the ethoxycarbonylmethyl radical ($CH_3CH_2OC(O)CH_2$—).

Phenyl-1–4C-alkyl represents one of the abovementioned 1–4C-alkyl radicals which is substituted by phenyl. Examples which may be mentioned are the phenethyl and the benzyl radicals.

Exemplary 1–4C-alkyl radicals substituted by R17 which may be mentioned are the 2-methoxycarbonylethyl, the 2-ethoxycarbonylethyl, the methoxycarbonylmethyl, the carboxymethyl, the 2-hydroxyethyl, the methoxymethyl, the 2-methoxyethyl, the 2-hydroxyethyl, the dimethylaminomethyl and the 2-dimethylaminoethyl radicals and, in particular, the pyridin-4-ylmethyl radical.

Possible radicals —$C_mH_{2m}$— are straight-chain or branched radicals. Examples which may be mentioned are the heptylene, isoheptylene (2-methylhexylene), hexylene, isohexylene (2-methylpentylene), neohexylene (2,2-dimethylbutylene), pentylene, isopentylene (3-methylbutylene), neopentylene (2,2-dimethylpropylene), butylene, iso-butylene, sec-butylene, tert-butylene, propylene, isopropylene, ethylene and methylene radicals. Radicals —$C_mH_{2m}$— preferably to be mentioned are the methylene (—$CH_2$—), the ethylene (—$CH_2CH_2$—), the butylene (—$CH_2CH_2CH_2CH_2$—) and the propylene (—$CH_2CH_2CH_2$—) radicals.

Possible radicals —$C_nH_{2n}$— are likewise straight-chain or branched radicals. Examples which may be mentioned are the butylene, iso-butylene, sec-butylene, tert-butylene, propylene, isopropylene, ethylene and methylene radicals. Radicals —$C_nH_2$— preferably to be mentioned are the methylene (—$CH_2$—) and ethylene (—$CH_2CH_2$—) radicals.

In one embodiment, n is the number 0 so that (with the condition that u is the number 1) the expression —$C_nH_{2n}$— is a bonding dash and the radical G is bonded directly to the group Z. This embodiment relates to those compounds in which G is hydrogen or a radical which is bonded to Z via a carbon atom.

In a further embodiment t is the number 0, so that the expression Y—$C_mH_{2m}$ is a bonding dash.

In a further embodiment u is the number 0, so that the expression Z—$C_nH_{2n}$ is a bonding dash.

The person skilled in the art is aware on account of his/her expert knowledge that certain combinations and conformations of X, A, Y, Z, G, m, n, t and u would lead to chemically less stable compounds. This applies in particular to those compounds in which two hetero-atoms (S, O or N) would directly meet or would only be separated by one carbon atom. Those compounds according to the invention which do not have the abovementioned conformations are therefore preferred.

The substituents R12 and R13 can be bonded to the cyclic systems or bicyclic systems G in any conceivable position, it being possible for the substituted or unsubstituted cyclic systems or bicyclic systems G themselves to be linked to the remainder of the molecule in any conceivable position. Exemplary radicals G which may be mentioned which are unsubstituted or substituted by R12 and R13 are: phenyl, 4-methylphenyl, 3dimethylaminomethylphenyl, 3-piperidinomethylphenyl, 3-carboxymethylphenyl, 2-dimethylaminomethyl-5-methyl-3-furyl, pyrrol-1-yl, 1-methylpyrrol-3-yl, 4,5-dimethyloxazol-2-yl, 3,5-dimethylisoxazol-4-yl, 4,5-dimethylthiazol-2-yl, 4-methyl-5-carboxymethylthiazol-2-yl, 1-methylimidazol-2-yl, 1-methylpyrazol-3-yl, 1-(2-dimethylaminoethyl)pyrazol-3-yl, 5-methyl-1,3,4-oxadiazol-2-yl, 1,2,4-triazol-1-yl, 1,2,4-triazol-2-yl, 1-methyl-1,2,3-triazol-4-yl, 1-methyl-1,2,4-triazol-3-yl, 1-(2-dimethylaminoethyl)-1,2,3-triazol-4-yl, 1-methyltetrazol-5-yl, 1-(2-dimethylaminoethyl)tetrazol-5-yl, 1-carboxymethyltetrazol-5-yl, 5-methyl-1,3,4-thiadiazol-2-yl, 5-trifluoromethyl-1,3,4-thiadiazol-2-yl, 1-(2-hydroxyethyl)tetrazol-5-yl, 2-amino-1,3,4-thiadiazol-2-yl, 3-amino-1,2,4-triazol-5-yl, 4-methyl-5-trifluoromethyl-1,2,4-triazol-3-yl, 4-aminopyrimidin-2-yl, 2-furyl, 3-furyl, 3methyl-2-furyl, 2-methyl-3-furyl, 5-methyl-2-furyl, 5-ethyl-2-furyl, 3-methoxy-2-furyl, 5-dimethylaminomethyl-2-furyl, 5-N-morpholinomethyl-2-furyl, 5-methoxymethyl-2-furyl, 5-hydroxymethyl-2-furyl, 5-N-piperidinomethyl-2-furyl, 5-chloro-2-furyl, 5-fluoro-2-furyl, 2-thienyl, 3-thienyl, 5-methyl-2-thienyl, 5-chloro-2-thienyl, 3-methyl-2-thienyl, 3-amino-2-thienyl, 3-guanidino-2-thienyl, 3-methoxy-2-thienyl, 2-methyl-3-thienyl, 5-dimethylaminomethyl-2-thienyl, 5-N-morpholinomethyl-2-thienyl, 5-methyl-2-pyrrolyl, 2,5-dimethyl-1-pyrrolyl, 1,5-dimethyl-2-pyrrolyl, 1-methyl-2-pyrrolyl, 2-thiazolyl, 4-thiazolyl, 5-thiazolyl, 2-amino-4-thiazolyl, 2-methyl-4-thiazolyl, 2-amino-5-methyl-4-thiazolyl, 4-methyl-5-thiazolyl, 2-dimethylaminomethyl-4-thiazolyl, 2-guanidino-4-thiazolyl, 2-formylamino-4-thiazolyl, 2-N-morpholinomethyl-4-thiazolyl, 4-methyl-5-oxazolyl, 3-guanidino-1-pyrazolyl, 3-guanidino-4-pyrazolyl, 1-imidazolyl, 2-imidazolyl, 4-imidazolyl, 2-methyl-4-imidazolyl, 5-methyl-4-imidazolyl, 2-methyl-1-imidazolyl, 2-methyl-5-nitro-1-imidazolyl, 4,5-dimethyl-2-imidazolyl, 4-hydroxymethyl-5-methyl-1-imidazolyl, 3-methyl-1 -pyrazolyl, 5-amino-1,2,4-thiadiazol-3-yl, 4-methoxy-2-pyridinyl, 4-methoxy-3-methyl-2-pyridinyl, 4-pyridinyl, 2-pyrimidinyl, 5-chloro-4-pyrimidinyl, 5-chloro-2,6-dimethyl-4-pyrimidinyl, 2-nitro-1-imidazolyl, 3,4-dimethoxypyridinyl, 1H-benzimidazol-2-yl, 6-imidazo[1,2-b]pyridazinyl and 3-nitro-6-imidazo[1,2-b]pyridazinyl.

Exemplary phenyl radicals which may be mentioned which are substituted by R14, R15 and R16 are the radicals 3,4-dihydroxy, 3-hydroxy-4-methoxy, 3,4-dimethoxy, 2-methoxy, 2-ethoxy, 3-methoxy, 4-methoxy, 2-hydroxy, 3-hydroxy, 4-hydroxy, 3,4-dihydroxy, 4-acetyl, 4-fluoro, 4-chloro, 2-chloro, 3-chloro, 3,4-dichloro, 3-trifluoromethyl, 2-trifluoromethyl, 2-methyl, 3-methyl, 4-methyl, 2,3-dimethyl, 2,4-dimethyl, 3,4-dimethyl, 2,5-dimethyl, 4-nitro, 2,6-dinitro-4-trifluormethyl and 5-chloro-2-methylaminophenyl.

Examples of substituted pyrrolidino radicals which may be mentioned are the 2-methoxymethylpyrrolidino, 2-methoxycarbonylpyrrolidino, 2-methylpyrrolidino, 2,5-dimethylpyrrolidino, 2-carboxypyrrolidino, 4-hydroxy-2-methoxycarbonylpyrrolidino, 4-hydroxy-2-ethoxycarbonylpyrrolidino, 2-(2-hydroxyethyl)pyrrolidino, 4-hydroxy-2-carboxypyrrolidino, 2-hydroxymethylpyrrolidino, 3-hydroxypyrrolidino and the 4-acetoxy-2-carboxypyrrolidino radicals.

Examples of substituted piperidino radicals which may be mentioned are the 2-carboxypiperidino, 2-n-propylpiperidino, 5-ethyl-2-methylpiperidino, 4-hydroxymethyl-4-phenylpiperidino, 4-n-propylpiperidino, 4-(3-phenylpropyl)piperidino, 2,6-dimethylpiperidino, 4-phenyl-4-propyloxycarbonylpiperidino, 4-ethoxycarbonyl-4-phenylpiperidino, 4-carboxy4-phenylpiperidino, 4-carboxypiperidino, 4-(4-fluorobenzoyl)piperidino, 4-(4-chlorobenzoyl)piperidino, 2,3-dicarboxypiperidino, 2,4-dicarboxypiperidino, 2,6-dicarboxypiperidino, 2-ethoxycarbonylpiperidino, 2-methylpiperidino, 2,6-dimethylpiperidino, 2-hydroxymethylpiperidino, 2-ethylpiperidino, 2-(2-hydroxyethyl)piperidino, 3-ethoxycarbonylpiperidino and the 4-benzylpiperidino radicals.

Examples of substituted piperazino radicals which may be mentioned are the 4-methylpiperazino, 4-phenylpiperazino, 4-(2-methylphenyl)piperazino, 4-(2,3-dimethylphenyl)piperazino, 4-(2-chlorophenyl)piperazino, 4-(2-methoxyphenyl)piperazino, 4-(2-ethoxyphenyl)piperazino, 4-(3-chlorophenyl)piperazino, 4-(4-fluorophenyl)piperazino, 4-(4-chlorophenyl)piperazino, 4-(4-methoxyphenyl)piperazino, 4-carbamoylpiperazino, 3-methyl-4-(4-chlorophenyl)piperazino, 3-methyl-4-(4-methoxyphenyl)piperazino, 3-methyl-4-(4-methylphenyl)piperazino, 4-(2,4-dimethylphenyl)piperazino, 4-(3,4-dichlorophenyl)piperazino, 4-(3,4-dimethylphenyl)piperazino, 3-methyl-4-phenylpiperazino, 3-methyl-4-(3-chlorophenyl)piperazino, 4-benzylpiperazino, 4-propylpiperazino, 4-(3-methylphenyl)piperazino, 4-(3-methoxyphenyl)piperazino, 4-(4-methylphenyl)piperazino, 4-(2,5-dimethylphenyl)piperazino, 4-cyclopropylpiperazino, 4-cyclobutylpiperazino, 4-cyclopentylpiperazino, 4-cyclohexylpiperazino, 4-cycloheptylpiperazino, 4-n-butylpiperazino, 4-isobutylpiperazino, 4-tert-butylpiperazino, 4-(1-phenylethyl)piperazino, 4-ethoxycarbonylmethylpiperazino, 4-(2-phenylethyl)piperazino, 4-(2-cyclohexylethyl)piperazino, 4-(2-hydroxyphenyl)piperazino, 4-(3,4-dimethoxyphenyl)piperazino, 4-isopropylpiperazino, 3-methyl-4-(3-methoxyphenyl)piperazino, 4-(4-hydroxyphenyl)piperazino, 3-methyl-4-(3-methylphenyl)piperazino, 4-(3-hydroxyphenyl)piperazino, 4-(2,6-dinitro-4-trifluoromethylphenyl)piperazino, 4-(4-nitrophenyl)piperazino, 4-(4-acetylphenyl)piperazino, 4-(2-chloro-5-thienylmethyl)piperazino and the 4-[2-(2-methyl-5-nitro-1-imidazolyl)ethyl]piperazino radicals.

An example of a substituted morpholino radical which may be mentioned is the 3,5-dimethylmorpholino radical.

An example of a substituted thiomorpholino radical which may be mentioned is the 2-carboxythiomorpholino radical.

Examples of substituted indolin-1-yl radicals which may be mentioned are the 2-carboxy-1-indolinyl, 6-fluoro-1-indolinyl, 5-bromo-1-indolinyl, 2,7-dimethyl-1-indolinyl, 2-methyl-1-indolinyl, 5-bromo-7-nitro-1-indolinyl, 5-nitro-1-indolinyl, 2,3-dimethyl-1-indolinyl and the 6-nitro-1-indolinyl radicals.

Examples of substituted 1,2,3,4-tetrahydroquinoline radicals which may be mentioned are the 2-ethoxycarbonyl-1,2,3,4-tetrahydro-1-quinolinyl, 2-methyl-1,2,3,4-tetrahydro-1-quinolinyl, 6-methyl-1,2,3,4-tetrahydro-1-quinolinyl, 6-fluoro-2-methyl-1,2,3,4-tetrahydro-1-quinolinyl, 4-methyl-1,2,3,4-tetrahydro-1-quinolinyl and the 2-fluoro-6-methyl-1,2,3,4-tetrahydro-1-quinolinyl radicals.

An example of a substituted 1,2,3,4-tetrahydroisoquinoline radical which may be mentioned is the 3-carboxy-1,2,3,4-tetrahydro-2-isoquinolinyl radical.

Examples of pyrimidin-4-yl radicals which may be mentioned are the 2,6-dimethylpyrimidin-4-yl, 2,6-dichloropyrimidin-4-yl, 2-chloro-5-fluoropyrimidin-4-yl and the 5-chloropyrimidin-4-yl radicals and in particular the 5-chloro-2,6-dimethylpyrimidin-4-yl radical.

Suitable salts of compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids can be employed in salt preparation—depending on whether it is a mono- or polybasic acid and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in an equimolar quantitative ratio or one differing therefrom.

Pharmacologically intolerable salts which can be initially obtained, for example, as process products in the preparation of the compounds according to the invention on an industrial scale, are converted into pharmacologically tolerable salts by processes known to the person skilled in the art.

It is known to the person skilled in the art that the compounds according to the invention, as well as their salts, if they are isolated, for example, in crystalline form, can contain various amounts of solvents. The invention therefore also includes all solvates and in particular all hydrates of the compounds of the formula I, and all solvates and in particular all hydrates of the salts of the compounds of the formula I.

One embodiment (embodiment a) of the invention relates to compounds of the formula I in which A is 2–7C-alkylene, X is O (oxygen) and Y is S, t is the number 1 and u is the number 0.

A further embodiment (embodiment b) of the invention relates to compounds of the formula I in which A is 2–7C-alkylene, X is S and Y is S, t is the number 1 and u is the number 0.

A further embodiment (embodiment c) of the invention relates to compounds of the formula I in which A is 2–7C-alkylene, X is S and Y is 1,4-piperazinylene, t is the number 1 and u is the number 0.

A further embodiment (embodiment d) of the invention relates to compounds of the formula I in which A is 1–7C-alkylene, X is S and t and u are the number 0.

A further embodiment (embodiment e) of the invention relates to compounds of the formula I in which A is 2–7C-alkylene, X is S and Z is S, n and t are the number 0 and u is the number 1.

A further embodiment (embodiment f) of the invention relates to compounds of the formula I in which A is 2–7C-alkylene, X is S and Y is 1,4-piperazinylene, t is the number 1 and u is the number 0 and G is

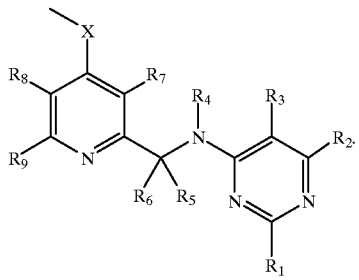

A further embodiment (embodiment g) of the invention relates to compounds of the formula I in which A is 1–7C-alkylene, X is O (oxygen) and t and u are the number 0.

A further embodiment (embodiment h) of the invention relates to compounds of the formula I in which A is 2–7C-alkylene, X is O (oxygen) and Y is 1,4-piperazinyl, t is the number 1 and u is the number 0.

A further embodiment (embodiment i) of the invention relates to compounds of the formula I in which A is 2–7C-alkylene, X is S and Z is NH, n and t are the number 0 and u is the number 1.

A further embodiment (embodiment j) of the invention relates to compounds of the formula I in which A is 2–7C-alkylene, X is O (oxygen) and Z is S, n and t are the number 0 and u is the number 1.

A further embodiment (embodiment k) of the invention relates to compounds of the formula I in which A is 1–7C-alkylene, 2–7C-alkenylene, 3–7C-cycloalkylene or phenylene, t and u are the number 0 and G is hydrogen.

A further embodiment (embodiment l) of the invention relates to compounds of the formula I in which A is 2–7C-alkylene, X is N-1–4C-alkyl and Y is S, t is the number 1 and u is the number 0.

A further embodiment (embodiment m) of the invention relates to compounds of the formula I in which A is 2–7C-alkylene, X is S, Y is O (oxygen) and Z is O (oxygen), t and u are the number 1, m is a number from 2 to 7, n is the number 0 and G is 1–4C-alkyl which is completely or mainly substituted by fluorine.

A further embodiment (embodiment n) of the invention relates to compounds of the formula I in which A is 2–7C-alkylene, X is N-1–4C-alkyl and Z is O (oxygen), t and n are the number 0 and u is the number 1.

A further embodiment (embodiment o) of the invention relates to compounds of the formula I in which A is 2–7C-alkylene, X is N-1–4C-alkyl and Z is S, t and n are the number 0 and u is the number 1.

A further embodiment (embodiment p) of the invention relates to compounds of the formula I in which A is 2–7C-alkylene, X is S and Z is O (oxygen), t and n are the number 0 and u is the number 1.

A further embodiment (embodiment q) of the invention relates to compounds of the formula I in which A is 2–7C-alkylene, X is N-1–4C-alkyl and Z is O (oxygen), t and n are the number 0 and u is the number 1 and G is hydrogen.

A further embodiment (embodiment r) of the invention relates to compounds of the formula I in which A is 2–7C-alkylene, X is N-1–4C-alkyl and t and u are the number 0.

A further embodiment (embodiment s) of the invention relates to compounds of the formula I in which A is 2–7C-alkylene, X is O (oxygen), Y is C (oxygen), Z is S and t and u are the number 1.

A further embodiment (embodiment t) of the invention relates to compounds of the formula I in which A is 2–7C-alkylene, X is S, Y is S, Z is O (oxygen) and t and u are the number 1.

A further embodiment (embodiment u) of the invention relates to compounds of the formula I in which A is 2–7C-alkylene, X is O (oxygen), Y is S, Z is O (oxygen) and t and u are the number 1.

A further embodiment (embodiment v) of the invention relates to compounds of the formula I in which A is 2–7C-alkylene, X is S, Y is S, Z is S and t and u are the number 1.

A further embodiment (embodiment w) of the invention relates to compounds of the formula I in which A is 2–7C-alkylene, X is S, Y is O (oxygen), Z is S and t and u are the number 1.

A further embodiment (embodiment x) of the invention relates to compounds of the formula I in which A is 2–7C-alkylene, X is S, Y is O (oxygen), t is the number 1 and u is the number 0.

Compounds of the embodiments l, n, o, q and r which are particularly worthy of mention are those in which R7 is halogen, in particular chlorine.

Compounds of the embodiments e, i, j, n, o and p which are particularly worthy of mention are those in which G is 3-nitroimidazo[1,2-b]pyridazin-6-yl.

One group of compounds according to the invention are those compounds, in which G has the meaning hydroxyl or oxazolidinone or is a glucopyranoside radical and/or R17 denotes pyridinyl and/or t is the number 2.

Another group of compounds according to the invention are those compounds, in which the meaning of G is other than hydroxyl, oxazolidinone and other than that of a glucopyranoside radical, the meaning of R17 is other than pyridinyl and the meaning of t is other than the number 2.

Compounds according to the invention to be emphasized are those of the formula I in which R1, R2 and R3 are identical to or different from one another and are hydrogen, 1–4C-alkyl or chlorine, R4 is hydrogen, R5 is hydrogen, R6 is hydrogen, R7 is hydrogen, 1–4C-alkyl, 1–4C-alkoxy or halogen, R8 is hydrogen, R9 is hydrogen, A is 1–7C-alkylene, G is hydrogen, hydroxyl, 1–4C-alkyl which is completely or mainly substituted by fluorine, the radical —N(R10)R11,

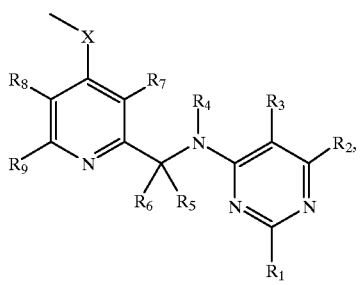

the glucopyranoside radical or a cyclic system or bicyclic system which is unsubstituted or substituted by R12 and R13 and which is selected from the group consisting of benzene, naphthalene, furan, thiophene, pyrrole, oxazole, oxazoline, oxazolidinone, isoxazole, thiazole, thiazoline, isothiazole, imidazole, imidazoline, pyrazole, triazole, tetrazole, thiadiazole, thiodiazole 1-oxide, oxadiazole, pyridine, pyridine N-oxide, pyrimidine, chloropyrimidine, piperidine, triazine, pyridone, benzimidazole, imidazopyridine, benzothiazole, benzoxazole, quinoline and imidazopyridazine,
in which
  R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, thiomorpholine, indoline, 1,2,3,4-tetrahydroquinoline and 1,2,3,4-tetrahydroisoquinoline, where
    a substituted pyrrolidino radical is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl,
    a substituted piperidino radical is substituted by one, two or three identical or different substituents selected from the group consisting of 1–4C-alkyl, 1–4C-alkoxycarbonyl, hydroxy-1–4C-alkyl, phenyl or phenyl-1–4C-alkyl, which is substituted by R14, R15 and R16, benzoyl, benzoyl substituted by halogen and carboxyl,
    a substituted piperazino radical can be substituted in the 2-, 3-, 5- or 6-position by a 1–4C-alkyl radical, and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl and carbamoyl,
    a substituted morpholino radical is substituted by one or two identical or different 1–4C-alkyl radicals,
    a substituted thiomorpholino radical is substituted by one or two identical or different 1–4C-alkyl radicals or a carboxyl group,
    a substituted indolin-1-yl radical can be substituted in the 2- and/or 3-position by a carboxyl group or by one or two identical or different 1–4C-alkyl radicals, and can be substituted in the benzo moiety by one or two identical or different substituents selected from the group consisting of 1–4C-alkyl, halogen and nitro,
    a substituted 1,2,3,4-tetrahydroquinoline radical is substituted by one or two identical or different substituents selected from the group consisting of 1–4C-alkyl, 1–4C-alkoxycarbonyl and halogen,
    a substituted 1,2,3,4-tetrahydroisoquinoline radical is substituted by one or two identical or different substituents selected from the group consisting of 1–4C-alkyl, carboxyl and phenyl,
  R12 is hydrogen, 1–4C-alkyl, hydroxyl, 1–4C-alkoxy, halogen, nitro, guanidino, carboxyl, 1–4C-alkoxycarbonyl, 1–4C-alkyl substituted by R17, phenyl substituted by R14, R15 and R16 or —N(R18)R19,
  R13 is hydrogen, 1–4C-alkyl, hydroxyl, 1–4C-alkoxy, halogen or trifluoromethyl,
  R14 is hydrogen, 1–4C-alkyl, hydroxyl, 1–4C-alkoxy, 1–4C-alkylcarbonyl, halogen, trifluoromethyl, 1–4C-alkylamino or nitro,
  R15 is hydrogen, 1–4C-alkyl, hydroxyl, 1–4C-alkoxy, halogen or nitro, and
  R16 is hydrogen or trifluoromethyl,
  R17 is hydroxyl, 1–4C-alkoxy, carboxyl, 1–4C-alkoxycarbonyl, pyridinyl or —N(R18)R19,
where
  R18 is hydrogen, 1–4C-alkyl or —CO—R20 and
  R19 is hydrogen or 1–4C-alkyl,
or where
  R18 and R19, together and including the nitrogen atom to which both are bonded, are a piperidino or morpholino radical,
  R20 is hydrogen, 1–4C-alkyl or 1–4C-alkoxy,
  X is O (oxygen), N-1–4C-alkyl, NH or S,
  Y is O (oxygen), N-1–4C-alkyl, NH, S or 1,4-piperazinylene,
  Z is O (oxygen), N-1–4C-alkyl, NH or S,
  m is a number from 1 to 7,
  n is a number from 0 to 4,
  t is the number 0, 1 or 2 and
  u is the number 0 or 1,
and their salts.
Compounds according to the invention to be emphasized particularly are those of the formula I in which
  R1 is hydrogen or 1–4C-alkyl,
  R2 is hydrogen or 1–4C-alkyl,
  R3 is halogen,
  R4 is hydrogen,
  R5 is hydrogen,
  R6 is hydrogen,
  R7 is 1–4C-alkyl or halogen,
  R8 is hydrogen,
  R9 is hydrogen,
  A is 1–7C-alkylene,
  G is hydrogen, hydroxyl, 1–4C-alkyl which is completely or mainly substituted by fluorine, the radical —N(R10)R11, the glucopyranoside radical or a cyclic system which is unsubstituted or substituted by R12 and R13 and which is selected from the group consisting of benzene, furan, thiophene, oxazole, oxazoline, oxazolidinone, thiazole, imidazole, triazole, tetrazole, pyridine, pyrimidine, chloropyrimidine, piperidine and imidazopyridazine,
in which
  R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, 1,2,3, 4-tetrahydroquinoline and 1,2,3,4-tetrahydroisoquinoline, where
a substituted piperazino radical is substituted in the 4-position by a substituent selected from the group consisting of 1–4C-alkyl and carbamoyl, R12 is hydrogen, 1–4C-alkyl, hydroxyl, halogen, nitro, carboxyl, phenyl which is substituted by R14, R15 and R16, 1–4C-alkyl which is substituted by R17 or 1–4C-alkoxycarbonyl, R13 is hydrogen or 1–4C-alkyl, R14 is hydrogen, 1–4C-alkyl, hydroxyl or 1–4C-alkoxy, R15 is hydrogen and R16 is hydrogen, R17 is pyridinyl, X is O (oxygen), N-1–4C-alkyl or S, Y is O (oxygen), S or 1,4-piperazinylene, Z is O (oxygen), NH or S, m is a number from 1 to 4, n is a number from 0 to 2, t is the number 0, 1 or 2 and u is the number 0 or 1, and their salts.

Preferred compounds according to the invention are those of the formula I in which R1 is hydrogen or 1–4C-alkyl, R2 is hydrogen or 1–4C-alkyl, R3 is chlorine, R4 is hydrogen, R5 is hydrogen, R6 is hydrogen, R7 is 1–4C-alkyl or chlorine, R8 is hydrogen, R9 is hydrogen, A is 1–4C-alkylene, G is hydrogen, 1–4C-alkyl which is completely or mainly substituted by fluorine, the radical —N(R10)R11 or a cyclic system which is unsubstituted or substituted by R12 and R13 and which is selected from the group consisting of furan, thiophene, oxazoline, oxazolidinone, imidazole, pyridine, pyrimidine, chloropyrimidine and piperidine, in which R10 and R11, together and including the nitrogen atom to which both are bonded, are a piperazine or 1,2,3,4-tetrahydroisoquinoline radical, R12 is hydrogen, 1–4C-alkyl, nitro, phenyl which is substituted by R14, R15 and R16 or 1–4C-allyl which is substituted by R17, R13 is hydrogen or 1–4C-alkyl, R14 is hydrogen or 1–4C-alkoxy, R15 is hydrogen and R16 is hydrogen, R17 is pyridinyl, X is O (oxygen), N-1–4C-alkyl or S, Y is O (oxygen), S or 1,4-piperazinylene, Z is O (oxygen), NH or S, m is a number from 1 to 4, n is a number from 0 to 2, t is the number 0 or 1 and u is the number 0 or 1, and their salts.

Preferred embodiments of the invention are those of embodiments a to x, in which the substituents and symbols have the meanings of the preferred compounds according to the invention.

Exemplary compounds according to the invention are listed in the following tables:

TABLE 1

Compounds of the formula I in embodiment a (see above) with R1 = $CH_3$, R2 = $CH_3$, R3 = Cl, R4, R5, R6, R8 and R9 = H, R7 = $CH_3$ and the following further substituents and symbol meanings:

| A | m | G |
|---|---|---|
| —$(CH_2)_2$— | 2 | 2-Methyl-5-nitroimidazol-1-yl |
| —$(CH_2)_2$— | 3 | 2-Methyl-5-nitroimidazol-1-yl |
| —$(CH_2)_2$— | 4 | 2-Methyl-5-nitroimidazol-1-yl |
| —$(CH_2)_3$— | 2 | 2-Methyl-5-nitroimidazol-1-yl |
| —$(CH_2)_3$— | 3 | 2-Methyl-5-nitroimidazol-1-yl |
| —$(CH_2)_3$— | 4 | 2-Methyl-5-nitroimidazol-1-yl |
| —$(CH_2)_4$— | 2 | 2-Methyl-5-nitroimidazol-1-yl |
| —$(CH_2)_4$— | 3 | 2-Methyl-5-nitroimidazol-1-yl |
| —$(CH_2)_4$— | 4 | 2-Methyl-5-nitroimidazol-1-yl |
| —$(CH_2)_5$— | 2 | 2-Methyl-5-nitroimidazol-1-yl |
| —$(CH_2)_5$— | 3 | 2-Methyl-5-nitroimidazol-1-yl |
| —$(CH_2)_6$— | 2 | 2-Methyl-5-nitroimidazol-1-yl |
| —$(CH_2)_2$— | 1 | 4-Pyridinyl |
| —$(CH_2)_2$— | 2 | 4-Pyridinyl |
| —$(CH_2)_2$— | 3 | 4-Pyridinyl |
| —$(CH_2)_2$— | 4 | 4-Pyridinyl |
| —$(CH_2)_3$— | 1 | 4-Pyridinyl |
| —$(CH_2)_3$— | 2 | 4-Pyridinyl |
| —$(CH_2)_3$— | 3 | 4-Pyridinyl |
| —$(CH_2)_3$— | 4 | 4-Pyridinyl |
| —$(CH_2)_4$— | 1 | 4-Pyridinyl |
| —$(CH_2)_4$— | 2 | 4-Pyridinyl |
| —$(CH_2)_4$— | 3 | 4-Pyridinyl |
| —$(CH_2)_4$— | 4 | 4-Pyridinyl |
| —$(CH_2)_5$— | 1 | 4-Pyridinyl |
| —$(CH_2)_5$— | 2 | 4-Pyridinyl |
| —$(CH_2)_5$— | 3 | 4-Pyridinyl |
| —$(CH_2)_6$— | 1 | 4-Pyridinyl |
| —$(CH_2)_6$— | 2 | 4-Pyridinyl |
| —$(CH_2)_2$— | 1 | 2-Pyrimidinyl |
| —$(CH_2)_2$— | 2 | 2-Pyrimidinyl |
| —$(CH_2)_2$— | 3 | 2-Pyrimidinyl |
| —$(CH_2)_2$— | 4 | 2-Pyrimidinyl |
| —$(CH_2)_3$— | 1 | 2-Pyrimidinyl |
| —$(CH_2)_3$— | 2 | 2-Pyrimidinyl |
| —$(CH_2)_3$— | 3 | 2-Pyrimidinyl |
| —$(CH_2)_3$— | 4 | 2-Pyrimidinyl |
| —$(CH_2)_4$— | 1 | 2-Pyrimidinyl |
| —$(CH_2)_4$— | 2 | 2-Pyrimidinyl |
| —$(CH_2)_4$— | 3 | 2-Pyrimidinyl |
| —$(CH_2)_4$— | 4 | 2-Pyrimidinyl |
| —$(CH_2)_5$— | 1 | 2-Pyrimidinyl |
| —$(CH_2)_5$— | 2 | 2-Pyrimidinyl |
| —$(CH_2)_5$— | 3 | 2-Pyrimidinyl |
| —$(CH_2)_6$— | 1 | 2-Pyrimidinyl |
| —$(CH_2)_6$— | 2 | 2-Pyrimidinyl |

TABLE 2

Compounds of the formula I in embodiment b (see above) with R1 = $CH_3$, R2 = $CH_3$, R3 = Cl, R4, R5, R6, R8 and R9 = H, R7 = $CH_3$ and the further substituents and symbol meanings for A, m and G as indicated in Table 1.

TABLE 3

Compounds of the formula I in embodiment c (see above) with R1 = $CH_3$, R2 = $CH_3$, R3 = Cl, R4, R5, R6, R8 and R9 = H, R7 = $CH_3$ and the further substituents and symbol meanings for A, m and G as indicated in Table 1.

TABLE 4

Compounds of the formula I in embodiment h (see above) with R1 = CH$_3$, R2 = CH$_3$, R3 = Cl, R4, R5, R6, R8 and R9 = H, R7 = CH$_3$ and the further substituents and symbol meanings for A, m and G as indicated in Table 1.

TABLE 5

Compounds of the formula I in embodiment l (see above) with R1 = CH$_3$, R2 = CH$_3$, R3 = Cl, R4, R5, R6, R8 and R9 = H, R7 = CH$_3$ and the further substituents and symbol meanings for A, m and G as indicated in Table 1.

TABLE 6

Compounds of the formula I in embodiment d (see above) with R1 = CH$_3$, R2 = CH$_3$, R3 = Cl, R4, R5, R6, R8 and R9 = H, R7 = CH$_3$ and the following further substituents and symbol meanings:

| A | G |
| --- | --- |
| —(CH$_2$)$_2$— | 2-Methyl-5-nitroimidazol-1-yl |
| —(CH$_2$)$_3$— | 2-Methyl-5-nitroimidazol-1-yl |
| —(CH$_2$)$_4$— | 2-Methyl-5-nitroimidazol-1-yl |
| —(CH$_2$)$_5$— | 2-Methyl-5-nitroimidazol-1-yl |
| —(CH$_2$)$_6$— | 2-Methyl-5-nitroimidazol-1-yl |
| —CH$_2$— | 4-Pyridinyl |
| —(CH$_2$)$_2$— | 4-Pyridinyl |
| —(CH$_2$)$_3$— | 4-Pyridinyl |
| —(CH$_2$)$_4$— | 4-Pyridinyl |
| —(CH$_2$)$_5$— | 4-Pyridinyl |
| —(CH$_2$)$_6$— | 4-Pyridinyl |
| —CH$_2$— | 2-Pyrimidinyl |
| —(CH$_2$)$_2$— | 2-Pyrimidinyl |
| —(CH$_2$)$_3$— | 2-Pyrimidinyl |
| —(CH$_2$)$_4$— | 2-Pyrimidinyl |
| —(CH$_2$)$_5$— | 2-Pyrimidinyl |
| —(CH$_2$)$_6$— | 2-Pyrimidinyl |

TABLE 7

Compounds of the formula I in embodiment g (see above) with R1 = CH$_3$, R2 = CH$_3$, R3 = Cl, R4, R5, R6, R8 and R9 = H, R7 = CH$_3$ and the further substituents and symbol meanings for A and G as indicated in Table 6.

TABLE 8

Compounds of the formula I in embodiment e (see above) with R1 = CH$_3$, R2 = CH$_3$, R3 = Cl, R4, R5, R6, R8 and R9 = H, R7 = CH$_3$ and the following further substituents and symbol meanings:

| A | G |
| --- | --- |
| —(CH$_2$)$_2$— | 4-Pyridinyl |
| —(CH$_2$)$_3$— | 4-Pyridinyl |
| —(CH$_2$)$_4$— | 4-Pyridinyl |
| —(CH$_2$)$_5$— | 4-Pyridinyl |
| —(CH$_2$)$_6$— | 4-Pyridinyl |
| —(CH$_2$)$_2$— | 2-Pyrimidinyl |
| —(CH$_2$)$_3$— | 2-Pyrimidinyl |
| —(CH$_2$)$_4$— | 2-Pyrimidinyl |
| —(CH$_2$)$_5$— | 2-Pyrimidinyl |
| —(CH$_2$)$_6$— | 2-Pyrimidinyl |
| —(CH$_2$)$_2$— | 3-Nitroimidazo[1,2-b]pyridazin-6-yl |
| —(CH$_2$)$_3$— | 3-Nitroimidazo[1,2-b]pyridazin-6-yl |
| —(CH$_2$)$_4$— | 3-Nitroimidazo[1,2-b]pyridazin-6-yl |
| —(CH$_2$)$_5$— | 3-Nitroimidazo[1,2-b]pyridazin-6-yl |
| —(CH$_2$)$_6$— | 3-Nitroimidazo[1,2-b]pyridazin-6-yl |

TABLE 9

Compounds of the formula I in embodiment i (see above) with R1 = CH$_3$, R2 = CH$_3$, R3 = Cl, R4, R5, R6, R8 and R9 = H, R7 = CH$_3$ and the further substituents and symbol meanings for A and G as indicated in Table 8.

TABLE 10

Compounds of the formula I in embodiment j (see above) with R1 = CH$_3$, R2 = CH$_3$, R3 = Cl, R4, R5, R6, R8 and R9 = H, R7 = CH$_3$ and the further substituents and symbol meanings for A and G as indicated in Table 8.

TABLE 11

Compounds of the formula I in embodiment n (see above) with R1 = CH$_3$, R2 = CH$_3$, R3 = Cl, R4, R5, R6, R8 and R9 = H, R7 = Cl and the further substituents and symbol meanings for A and G as indicated in Table 8.

TABLE 12

Compounds of the formula I in embodiment o (see above) with R1 = CH$_3$, R2 = CH$_3$, R3 = Cl, R4, R5, R6, R8 and R9 = H, R7 = Cl and the further substituents and symbol meanings for A and G as indicated in Table 8.

TABLE 13

Compounds of the formula I in embodiment p (see above) with R1 = CH$_3$, R2 = CH$_3$, R3 = Cl, R4, R5, R6, R8 and R9 = H, R7 = CH$_3$ and the further substituents and symbol meanings for A and G as indicated in Table 8.

TABLE 14

Compounds of the formula I in embodiment m (see above) with R1 = CH$_3$, R2 = CH$_3$, R3 = Cl, R4, R5, R6, R8 and R9 = H, R7 = CH$_3$ and the following further substituents and symbol meanings:

| A | m | G |
| --- | --- | --- |
| —(CH$_2$)$_2$— | 2 | 2,2,2-Trifluoroethyl |
| —(CH$_2$)$_2$— | 3 | 2,2,2-Trifluoroethyl |
| —(CH$_2$)$_2$— | 4 | 2,2,2-Trifluoroethyl |
| —(CH$_2$)$_3$— | 2 | 2,2,2-Trifluoroethyl |
| —(CH$_2$)$_3$— | 3 | 2,2,2-Trifluoroethyl |
| —(CH$_2$)$_3$— | 4 | 2,2,2-Trifluoroethyl |
| —(CH$_2$)$_4$— | 2 | 2,2,2-Trifluoroethyl |
| —(CH$_2$)$_4$— | 3 | 2,2,2-Trifluoroethyl |
| —(CH$_2$)$_4$— | 4 | 2,2,2-Trifluoroethyl |
| —(CH$_2$)$_5$— | 1 | 2,2,2-Trifluoroethyl |
| —(CH$_2$)$_5$— | 2 | 2,2,2-Trifluoroethyl |
| —(CH$_2$)$_5$— | 3 | 2,2,2-Trifluoroethyl |

TABLE 14-continued

Compounds of the formula I in embodiment m (see above) with R1 = CH$_3$, R2 = CH$_3$, R3 = Cl, R4, R5, R6, R8 and R9 = H, R7 = CH$_3$ and the following further substituents and symbol meanings:

| A | m | G |
|---|---|---|
| —(CH$_2$)$_6$— | 1 | 2,2,2-Trifluoroethyl |
| —(CH$_2$)$_6$— | 2 | 2,2,2-Trifluoroethyl |
| —(CH$_2$)$_2$— | 2 | Trifluoromethyl |
| —(CH$_2$)$_2$— | 3 | Trifluoromethyl |
| —(CH$_2$)$_2$— | 4 | Trifluoromethyl |
| —(CH$_2$)$_3$— | 2 | Trifluoromethyl |
| —(CH$_2$)$_3$— | 3 | Trifluoromethyl |
| —(CH$_2$)$_3$— | 4 | Trifluoromethyl |
| —(CH$_2$)$_4$— | 2 | Trifluoromethyl |
| —(CH$_2$)$_4$— | 3 | Trifluoromethyl |
| —(CH$_2$)$_4$— | 4 | Trifluoromethyl |
| —(CH$_2$)$_5$— | 2 | Trifluoromethyl |
| —(CH$_2$)$_5$— | 3 | Trifluoromethyl |
| —(CH$_2$)$_6$— | 2 | Trifluoromethyl |
| —(CH$_2$)$_2$— | 2 | Difluoromethyl |
| —(CH$_2$)$_2$— | 3 | Difluoromethyl |
| —(CH$_2$)$_2$— | 4 | Difluoromethyl |
| —(CH$_2$)$_3$— | 2 | Difluoromethyl |
| —(CH$_2$)$_3$— | 3 | Difluoromethyl |
| —(CH$_2$)$_3$— | 4 | Difluoromethyl |
| —(CH$_2$)$_4$— | 2 | Difluoromethyl |
| —(CH$_2$)$_4$— | 3 | Difluoromethyl |
| —(CH$_2$)$_4$— | 4 | Difluoromethyl |
| —(CH$_2$)$_5$— | 2 | Difluoromethyl |
| —(CH$_2$)$_5$— | 3 | Difluoromethyl |
| —(CH$_2$)$_6$— | 2 | Difluoromethyl |

TABLE 15

Compounds of the formula I in embodiment q (see above) with R1 = CH$_3$, R2 = CH$_3$, R3 = Cl, R4, R5, R6, R8 and R9 = H and the following further substituents and symbol meanings:

| A | R7 |
|---|---|
| —(CH$_2$)$_2$— | CH$_3$ |
| —(CH$_2$)$_3$— | CH$_3$ |
| —(CH$_2$)$_4$— | CH$_3$ |
| —(CH$_2$)$_5$— | CH$_3$ |
| —(CH$_2$)$_6$— | CH$_3$ |
| —(CH$_2$)$_2$— | Cl |
| —(CH$_2$)$_3$— | Cl |
| —(CH$_2$)$_4$— | Cl |
| —(CH$_2$)$_5$— | Cl |
| —(CH$_2$)$_6$— | Cl |

TABLE 16

Compounds of the formula I in embodiment r (see above) with R1 = CH$_3$, R2 = CH$_3$, R3 = Cl, R4, R5, R6, R8 and R9 = H and the following further substituents and symbol meanings:

| A | R7 | G |
|---|---|---|
| —(CH$_2$)$_2$— | CH$_3$ | 1,2,3,4-Tetrahydroisoquinolin-2-yl |
| —(CH$_2$)$_3$— | CH$_3$ | 1,2,3,4-Tetrahydroisoquinolin-2-yl |
| —(CH$_2$)$_4$— | CH$_3$ | 1,2,3,4-Tetrahydroisoquinolin-2-yl |
| —(CH$_2$)$_5$— | CH$_3$ | 1,2,3,4-Tetrahydroisoquinolin-2-yl |
| —(CH$_2$)$_6$— | CH$_3$ | 1,2,3,4-Tetrahydroisoquinolin-2-yl |
| —(CH$_2$)$_2$— | Cl | 1,2,3,4-Tetrahydroisoquinolin-2-yl |
| —(CH$_2$)$_3$— | Cl | 1,2,3,4-Tetrahydroisoquinolin-2-yl |
| —(CH$_2$)$_4$— | Cl | 1,2,3,4-Tetrahydroisoquinolin-2-yl |
| —(CH$_2$)$_5$— | Cl | 1,2,3,4-Tetrahydroisoquinolin-2-yl |
| —(CH$_2$)$_6$— | Cl | 1,2,3,4-Tetrahydroisoquinolin-2-yl |
| —(CH$_2$)$_2$— | CH$_3$ | 6,7-Dimethoxy-1,2,3,4-tetrahydroisoquinolin-2-yl |
| —(CH$_2$)$_3$— | CH$_3$ | 6,7-Dimethoxy-1,2,3,4-tetrahydroisoquinolin-2-yl |
| —(CH$_2$)$_4$— | CH$_3$ | 6,7-Dimethoxy-1,2,3,4-tetrahydroisoquinolin-2-yl |
| —(CH$_2$)$_5$— | CH$_3$ | 6,7-Dimethoxy-1,2,3,4-tetrahydroisoquinolin-2-yl |
| —(CH$_2$)$_6$— | CH$_3$ | 6,7-Dimethoxy-1,2,3,4-tetrahydroisoquinolin-2-yl |
| —(CH$_2$)$_2$— | Cl | 6,7-Dimethoxy-1,2,3,4-tetrahydroisoquinolin-2-yl |
| —(CH$_2$)$_3$— | Cl | 6,7-Dimethoxy-1,2,3,4-tetrahydroisoquinolin-2-yl |
| —(CH$_2$)$_4$— | Cl | 6,7-Dimethoxy-1,2,3,4-tetrahydroisoquinolin-2-yl |
| —(CH$_2$)$_5$— | Cl | 6,7-Dimethoxy-1,2,3,4-tetrahydroisoquinolin-2-yl |
| —(CH$_2$)$_6$— | Cl | 6,7-Dimethoxy-1,2,3,4-tetrahydroisoquinolin-2-yl |

TABLE 17

Compounds of the formula I in embodiment s (see above) with R1 = CH$_3$, R2 = CH$_3$, R3 = Cl, R4, R5, R6, R8 and R9 = H, R7 = CH$_3$, n = 2 and the further substituents and symbol meanings for A, m and G as indicated in Table 1.

TABLE 18

Compounds of the formula I in embodiment t (see above) with R1 = CH$_3$, R2 = CH$_3$, R3 = Cl, R4, R5, R6, R8 and R9 = H, R7 = CH$_3$, n = 2 and the further substituents and symbol meanings for A, m and G as indicated in Table 1.

TABLE 19

Compounds of the formula I in embodiment u (see above) with R1 = CH$_3$, R2 = CH$_3$, R3 = Cl, R4, R5, R6, R8 and R9 = H, R7 = CH$_3$, n = 2 and the further substituents and symbol meanings for A, m and G as indicated in Table 1.

TABLE 20

Compounds of the formula I in embodiment v (see above) with R1 = CH$_3$, R2 = CH$_3$, R3 = Cl, R4, R5, R6, R8 and R9 = H, R7 = CH$_3$, n = 2 and the further substituents and symbol meanings for A, m and G as indicated in Table 1.

TABLE 21

Compounds of the formula I in embodiment w (see above) with R1 = CH$_3$, R2 = CH$_3$, R3 = Cl, R4, R5, R6, R8 and R9 = H, R7 = CH$_3$, n = 2 and the further substituents and symbol meanings for A, m and G as indicated in Table 1.

TABLE 22

Compounds of the formula I in embodiment x (see above) with R1 = CH$_3$, R2 = CH$_3$, R3 = Cl, R4, R5, R6, R8 and R9 = H and R7 = CH$_3$ and the further substituents and symbol meanings for A, m and G as indicated in Table 1.

and the salts of the compounds mentioned in Tables 1 to 22.

The compounds of the formula I according to the invention can be prepared in various ways. In principle, the compounds of the formula I can be prepared by reaction of the aminopyrimidines of the formula II with 2-halomethylpyridines of the formula III (Hal=halogen, in particular chlorine) in a manner known per se.

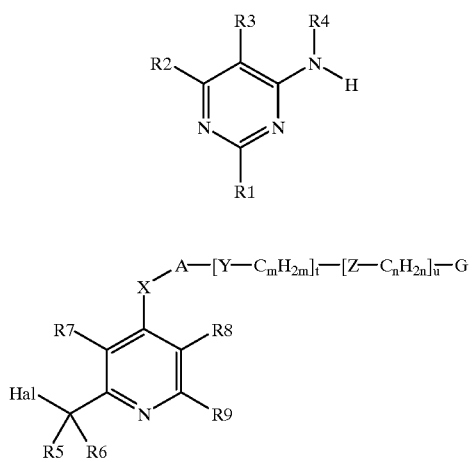

If appropriate, it may be useful to introduce the radical —X—A—[Y—C$_m$H$_{2m}$]$_t$—[Z—C$_n$H$_{2n}$]$_u$—G completely or partially into the 4-position of the pyridine only after the reaction of an appropriately substituted 2-halomethylpyridine with the aminopyrimidine 11. The manner in which the compounds according to the invention can be obtained is shown in exemplary form in the following examples.

The compounds of the formula II are known or can be prepared in a known manner analogously to known compounds.

The compounds of the formula III are also known (see, for example, the abovementioned International Patent Applications in the section "Known Technical Background") or the abovementioned complete or partial introduction of the radical —X—A—[Y—C$_m$H$_{2m}$]$_t$—[Z—C$_n$H$_{2n}$]$_u$—G is described in the International Patent Applications mentioned.

The following examples explain the invention in greater detail without restricting it. The exemplary final products and the salts of these compounds are preferred subject matter of the invention. The compounds according to the invention and the starting compounds can be prepared in a manner analogous to that described in the examples. The abbreviation m.p. means melting point, conc. stands for "concentrated", h stands for hour(s).

EXAMPLES

Final products 1. (3-Chloro-4-{[2-(3,4-dihydro-1H-isoquinolin-2-yl)ethyl]methylamino}pyridin-2-ylmethyl)-(5-chloro-2,6-dimethylpyrimidin-4-yl)amine 0.55 g (1.47 mmol) of {3-chloro-4-[(2-chloroethyl)methylamino]pyridin-2-ylmethyl}-(5-chloro-2,6-dimethylpyrimidin-4-yl)amine and 0.2 g (1.5 mmol) of 1,2,3,4-tetrahydroisoquinoline are dissolved in 2 ml of n-butanol and stirred at 120° C. for 48 h. The mixture is concentrated and taken up with 20 ml of half-saturated sodium hydrogencarbonate solution and 20 ml of ethyl acetate. The aqueous phase is extracted with 3×20 ml of ethyl acetate. The organic extracts are dried over magnesium sulfate and concentrated. 0.19 g (27%) of the title compound is obtained. M.p. 81° C.–93° C.

2. 2-({3-Chloro-2-[(5-chloro-2,6-dimethylpyrimidin-4-ylamino)methyl]pyridin-4-yl}methylamino)ethanol 2.2 g (13.9 mmol) of 4-amino-5-chloro-2,6-dimethylpyrimidine are dissolved in 20 ml of dimethylformamide under a nitrogen atmosphere and 1.8 g of sodium hydride (60% strength suspension) are added in portions with vigorous stirring. The suspension is stirred at room temperature for a further 0.5 h. A solution of 3.3 g (14.0 mmol) of 2-[(3-chloro-2-chloromethylpyridin-4-yl)methylamino]ethanol in dimethylformamide (10 ml) is then added dropwise in the course of 0.5 h and the mixture is stirred at room temperature for a further 0.5 h. The mixture is cooled to 0° C. and cautiously treated with water (200 ml) with vigorous stirring. It is then extracted with 3×50 ml of ethyl acetate. The organic extracts are washed with 50 ml of water, dried over magnesium sulfate and concentrated. The residue is purified by chromatography on silica gel (eluent: petroleum ether/ethyl acetate=4:1). The fractions of R$_f$=0.3 are concentrated. 1.1 g (22%) of the title compound are obtained as a colorless solid. M.p. 162° C.–165° C.

3. (5-Chloro-2,6-dimethylpyrimidin-4-yl)-{3-methyl-4-[3-(5-phenyl-1H-imidazol-2-ylsulfanyl)propylsulfanyl]pyridin-2-ylmethyl}amine hydrochloride 0.9 g (2.0 mmol) of 2-(3-{2-[(5-chloro-2,6-dimethylpyrimidin-4-ylamino)methyl]-3-methylpyridin-4-ylsulfanyl}propyl)isothiourea and 0.42 g (3.0 mmol) of potassium carbonate are suspended in 15 ml of ethanol and a solution of 0.43 g (2.1 mmol) of ω-bromoacetophenone in 8 ml of ethanol is added dropwise. The mixture is stirred at room temperature for 3 d. The mixture is then added to 100 ml of water and extracted with 3×40 ml of ethyl acetate. The organic extracts are washed With 50 ml of water, dried over magnesium sulfate and concentrated. The residue is purified by chromatography on silica gel (eluent: ethyl acetate/methanol=20:1+3% ammonia). The fractions of R$_f$=0.49 are concentrated. The residue is extracted by stirring with diisopropyl ether. After filtration, 0.14 g (14%) of the title compound is isolated as a colorless solid. M.p. 188° C.–190° C.

4. (5-Chloro-2,6-dimethylpyrimidin-4-yl)-(3-methyl-4-{2-[2-(2,2,2-trifluoroethoxy)ethoxy]ethylsulfanyl}pyridin-2-ylmethyl)amine hydrochloride 0.28 g of sodium hydride (60% strength suspension) is suspended in 8 ml of dimethylformamide under a nitrogen atmosphere. A solution of 0.62 g (3.93 mmol) of 4-amino-5-chloro-2,6-dimethylpyrimidine in dimethylformamide (5 ml) is then added dropwise at room temperature in the course of 0.5 h with vigorous stirring. The suspension is stirred at room temperature for a further 0.5 h. A solution of 0.84 g (2.44 mmol) of 2-chloromethyl-3-methyl-4-{2-[2-(2,2,2-trifluoroethoxy)ethoxy]ethylsulfanyl}pyridine in dimethylformamide (5 ml) is then added dropwise in the course of 0.5 h and the mixture is stirred at room temperature for a further 0.5 h. The mixture is cooled to 0° C. and cautiously treated with water (10 ml) with vigorous stirring. It is then extracted with 3×20 ml of ethyl acetate. The organic extracts are washed with 20 ml of water, dried over magnesium sulfate and concentrated. The residue is purified by chromatography on silica gel (eluent: toluene/ethyl acetate=1:1). The fractions of R$_f$=0.31 are concentrated and the residue is dissolved in isopropanol. It is then precipitated with ethereal hydrogen chloride solution. After filtration, the filtrate is concentrated. 0.5 g (41%) of the title compound is isolated as a colorless solid. M.p. 235° C.–241° C. (dec.).

5. 5-(3-{2-[(5-Chloro-2,6-dimethylpyrimidin-4-ylamino)methyl]-3-methylpyridin-4-ylsulfanyl}propylsulfanylmethyl)-3-methyloxazolidin-2-one 4.5 g (11.32 mmol) of 5-[3-(2-chloromethyl-3-methyl-pyridin-4-ylsulfanyl)propylsulfanylmethyl]-3-methyloxazolidin-2-one hydrochloride are dissolved in 30 ml of water and treated with 30 ml of dichloromethane. The pH is adjusted to a value of 8 with vigorous stirring using saturated sodium hydrogen-carbonate solution. The organic phase is separated off. The aqueous phase is extracted again with 30 ml of dichloromethane. The combined organic phases are dried over magnesium sulfate and concentrated, and the residue is taken up in 10 ml of dimethylformamide. This solution is added dropwise in the course of 20 minutes to a previously prepared solution of 2.73 g (16.98 mmol) of 4-amino-5-chloro-2,6-dimethylpyrimidine and 0.5 g (12.45 mmol) of sodium hydride (60% strength in paraffin) in 35 ml of dimethylformamide. The mixture is stirred at room temperature for 20 hours. Dimethylformamide is stripped off in a high vacuum and the residue is taken up in 100 ml of water. It is extracted three times with 25 ml of dichloromethane each time. The combined organic phases are concentrated. The residue is chromatographed on silica gel using ethyl acetate/methanol=15/1. The crude product is digested with diethyl ether. 3.13 g (57%) of the title compound are obtained as a crystalline solid. M.p. 121° C.

6. (5-Chloro-2,6-dimethylpyrimidin-4-yl)3-methyl-4-[4-(pyrimidin-2-ylsulfanyl)butoxy]-pyridin-2-ylmethyl}amine 1.2 g (3.24 mmol) of [4-(4-chlorobutoxy)-3-methyl-pyridin-2-ylmethyl]-(5-chloro-2,6-dimethylpyrimidin-4-yl) amine are refluxed in 30 ml of acetonitrile for 5 hours together with 0.41 g (3.57 mmol of 2-mercapto-pyrimidine and 0.67 g (6.48 mmol) of sodium carbonate. Acetonitrile is stripped off in vacuo and the residue is taken up in 70 ml of water. It is extracted three times with 30 ml of dichloromethane each time. The combined organic phases are concentrated. The residue is chromatographed on silica gel using toluene/ethyl acetate/methanol/conc. ammonia=6/3.5/0.5/0.05. The crude product is digested with diethyl ether. 1.25 g (87%) of the title compound are obtained as a crystalline solid. M.p. 112–114° C.

7. {4-[3-(5-Chloro-2,6-dimethylpyrimidin-4-ylamino)propylsulfanyl]-3-methylpyridin-2-ylmethyl}-(5-chloro-2,6-dimethylpyrimidin-4-yl)amine 30 g (104.28 mmol) of 2-chloromethyl-4-(3-chloropropylsulfanyl)-3-methylpyridine hydrochloride are dissolved in 100 ml of water and treated with saturated sodium hydrogencarbonate solution with stirring. The mixture is then extracted three times with 50 ml of dichloromethane each time. The combined organic phases are dried over magnesium sulfate and concentrated. The residue is dissolved in 15 ml of anhydrous DMF and added dropwise to a previously prepared solution of 20.12 g (125.13 mmol) of 4-amino-5-chloro-2,6-dimethylpyrimidine and 4.6 g (114.71 mmol) of sodium hydride (60% strength in paraffin) in 100 ml of anhydrous DMF. The mixture is stirred at room temperature for 20 hours. DMF is then stripped off in vacuo, the residue is taken up in 150 ml of water and the solution is extracted three times with 50 ml of dichloromethane each time. The combined organic phases are washed twice with water and concentrated. The residue is chromatographed on silica gel using toluene/ethyl acetate/methanol/conc. ammonia=6/3.6/0.4/0.05. The crude product is digested with diethyl ether. 7.82 g (14%) of the title compound are obtained as a crystalline solid. M.p. 170–174° C.

8. (5-Chloropyrimidin-4-yl)-{3-methyl-4-[3-(pyridin-4-ylmethylsulfanyl)propylsulfanyl]-pyridin-2-ylmethyl}amine 1.2 g (3.49 mmol) of [4-(3-chloropropylsulfanyl)-3-methylpyridin-2-ylmethyl]-(5-chloropyrimidin-4-yl)amine and 1.26 g (5.24 mmol) of 2-pyridin-4-ylmethylisothiuronium chloride are suspended in 30 ml of ethanol. 2.33 ml (13.96 mmol) of 6 N aqueous NaOH are added dropwise in the course of 20 minutes. The mixture is stirred at room temperature for 30 minutes and then heated at 60° C. for two hours. After cooling, it is diluted with 100 ml of water and extracted four times using 30 ml of dichloromethane each time. The combined organic phases are concentrated. The residue is chromatographed on silica gel using toluene/ethyl acetate/methanol/conc. ammonia=6/3.6/0.4/0.05. The crude product is digested with diethyl ether. 1.18 g (78%) of the title compound are obtained as a crystalline solid. M.p. 148–149° C.

9. (5-Chloropyrimidin-4-yl)-(3-methyl-4-{3-[2-(2-methyl-5-nitroimidazol-1-yl)ethylsulfanyl]propylsulfanyl}-pyridin-2-ylmethyl)amine 1.2 g (3.49 mmol) of [4-(3-chloropropylsulfanyl)-3-methylpyridin-2-ylmethyl)-(5-chloropyrimidin-4-yl)amine and 1.39 g (5.24 mmol) of 2-[2-(2-methyl-5-nitroimidazol-1-yl)ethyl]isothiuronium chloride are suspended in 30 ml of ethanol. 1.75 ml (10.47 mmol) of 6 N aqueous NaOH are added dropwise in the course of 20 minutes. The mixture is stirred at room temperature for 30 minutes and then heated at 60° C. for five hours. After cooling, it is diluted with 100 ml of water and extracted three times using 30 ml of ethyl acetate each time. The combined organic phases are concentrated. The residue is chromatographed on silica gel using toluene/ethyl acetate/methanol/conc. ammonia=6/3.6/0.4/0.05. The crude product is digested with diethyl ether. 0.81 g (47%) of the title compound is obtained as a crystalline solid. M.p. 119–121° C.

10. (5-Chloro-2,6-dimethylpyrimidin-4-yl)-{3-methyl-4-[3-(pyrimidin-2-ylsulfanyl)propylsulfanyl]-pyridin-2-ylmethyl}amine 1 g (2.69 mmol) of [4-(3-chloropropylsulfanyl)-3-methylpyridin-2-ylmethyl]-(5-chloro-2,6-dimethylpyrimidin-4-yl)amine is refluxed in 30 ml of acetonitrile for 4 hours together with 0.34 g (2.96 mmol) of 2-mercaptopyrimidine and 0.57 g (5.38 mmol) of sodium carbonate. Acetonitrile is stripped off in vacuo and the residue is taken up in 75 ml of water. It is extracted three times using 25 ml of dichloromethane/methanol=10/1 each time. The combined organic phases are concentrated. The residue is chromatographed on silica gel using dichloromethane/methanol/triethylamine=10/1/0.1. The crude product is digested with diethyl ether. 1.04 g (87%) of the title compound are obtained as a crystalline solid. M.p. 158–159° C.

11. (5-Chloro-2,6-dimethylpyrimidin-4-yl)-{3-methyl-4-[4-(4-pyridin-4-ylmethylpiperazin-1-yl)butoxy]pyridin-2-ylmethyl}amine 1.5 g (3.58 mmol) of (5-chloro-2,6-dimethylpyrimidin-4-yl)-[3-methyl-4-(4-piperazin-1-ylbutoxy)pyridin-2-y)

methyl]amine are refluxed in 30 ml of acetone for 6 hours together with 0.84 g (5.12 mmol) of 4-chloromethylpyridine hydrochloride, 1.14 g (10.74 mmol) of sodium carbonate and a catalytic amount of sodium iodide. Acetone is stripped off in vacuo and the residue is taken up in 100 ml of water. It is extracted four times using 25 ml of dichloromethane/methanol=10/1 each time. The combined organic phases are concentrated. The residue is chromatographed on silica gel using dichloromethane/methanol/triethylamine=10/1/0.1. The crude product is digested with diethyl ether. 1.34 g (73%) of the title compound are obtained as a crystalline solid. M.p. 157–158° C.

12. (5-Chloro-2,6-dimethylpyrimidin-4-yl)-{3-methyl-4-[4-(4-pyridin-4-ylmethylpiparazin-1-yl)butylsulfanyl]pyridin-2-ylmethyl}amine 1 g (2.29 mmol) of (5-chloro-2,6-dimethylpyrimidin-4-yl)-[3-methyl-4-(4-piperazin-1-ylbutylsulfanyl)pyridin-2-ylmethyl]amine is refluxed in 30 ml of acetone for 5 hours together with 0.41 g (2.41 mmol) of 4-chloromethylpyridine hydrochloride, 0.73 g (6.87 mmol) of sodium carbonate and a catalytic amount of sodium iodide. Acetone is stripped off in vacuo and the residue is taken up in 100 ml of water. It is extracted four times using 25 ml of dichloromethane/methanol=10/1 each time. The combined organic phases are concentrated. The residue is chromatographed on silica gel using dichloromethane/methanol/triethylamine=10/1/0.1. The crude product is digested with diethyl ether. 0.96 g (80%) of the title compound is obtained as a crystalline solid. M.p. 139–140° C.

13. 1,4-Bis{4-[(3-methyl-4-ylsulfanylpyridin-2-ylmethyl)-5-chloro-2,6-dimethylpyrimidin-4-ylamino]butyl}piperazine 2.25 g (5.84 mmol) of [4-(4-chlorobutylsulfanyl)-3-methylpyridin-2-ylmethyl]-(5-chloro-2,6-dimethylpyrimidin-4-yl)amine are refluxed in 30 ml of acetonitrile for 10 days together with 0.51 g (5.84 mmol) of piperazine, 1.24 g (11.67 mmol) of sodium carbonate and a catalytic amount of sodium iodide. The mixture is then stirred at room temperature for two days. Acetonitrile is stripped off in vacuo and the residue is taken up in 150 ml of water. It is extracted three times using 50 ml of dichloromethane/methanol=15/1 each time. The combined organic phases are washed twice with water and concentrated. The residue is chromatographed on silica gel using chloroform/methanol/conc. ammonia=10/2/0.05. The crude product is digested with diethyl ether. 0.84 g (55%) of the title compound is obtained as a crystalline solid. M.p. 188–190° C.

14. (5-Chloro-2,6-dimethylpyrimidin-4-yl)-[3-methyl-4-(4-piperazin-1-ylbutoxy)pyridin-2-ylmethyl]amine 5 g (13.53 mmol) of [4-(4-chlorobutoxy)-3-methylpyridin-2-ylmethyl]-(5-chloro-2,6-dimethylpyrimidin-4-yl)amine are refluxed in 100 ml of acetonitrile for 72 hours together with 7.0 g (81.23 mmol) of piperazine, 4.30 g (4 0.59 mmol) of sodium carbonate and a catalytic amount of sodium iodide. The mixture is then stirred at room temperature for two days. Acetonitrile is stripped off in vacuo and the residue is taken up in 150 ml of water. It is extracted five times using 50 ml of dichloromethane/methanol=10/1 each time. The combined organic phases are washed twice with water and concentrated. The residue is chromatographed on silica gel using dichloromethane/methanol/triethylamine=10/2/0.1. The crude product is digested with diethyl ether. 3.4 g (60%) of the title compound are obtained as a crystalline solid. M.p. 140–144° C.

15. (5-Chloro-2,6-dimethylpyrimidin-4-yl)-{3-methyl-4-[4-(piridin-4-ylmethylsulfanyl)-butoxy]pyridin-2-ylmethyl}amine 1.5 g (4.06 mmol) of (4-(4-chlorobutoxy)-3-methylpyridin-2-ylmethyl]-(5-chloro-2,6-dimethylpyrimidin-4-yl)amine and 1.46 g (6.09 mmol) of 2-pyridin-4-ylmethylisothiuronium chloride are suspended in 30 ml of ethanol. 2.53 ml (15.18 mmol) of 6 N aqueous NaOH are added dropwise in course of 30 minutes. The mixture is stirred at room temperature for 30 minutes and then heated at 60° C. for 5 hours. After cooling, it is diluted with 100 ml of water and extracted four times using 25 ml of ethyl acetate each time. The combined organic phases are washed once with water and concentrated. The residue is chromatographed on silica gel using toluene/ethyl acetate/methanol/conc. ammonia=6/3.5/0.5/0.05. The crude product is digested with diethyl ether. 1.15 g (62%) of the title compound are obtained as a crystalline solid. M.p. 90–92° C.

16. (5-Chloro-2,6-dimethylpyrimidin-4-yl)-(3-methyl-4-{4-[2-(2-methyl-5-nitroimidazol-1-yl)-ethylsulfanyl]butoxy}pyridin-2-ylmethyl]amine 1.5 g (4.06 mmol) of [4-(4-chlorobutoxy)-3-methylpyridin-2-ylmethyl]-(5-chloro-2,6-dimethylpyrimidin-4-yl)amine and 2.02 g (7.60 mmol) of 2-[2-(2-methyl-5-nitroimidazol-1-yl)ethyl]isothiuronium chloride are suspended in 30 ml of ethanol. 2.53 ml (15.18 mmol) of 6 N aqueous NaOH are added dropwise in the course of 30 minutes. The mixture is stirred at room temperature for 30 minutes and then heated at 60° C. for 5 hours. After cooling, it is diluted with 100 ml of water and extracted three times using 20 ml of ethyl acetate each time. The combined organic phases are washed once with water and concentrated. The residue is chromatographed on silica gel using toluene/ethyl acetate/methanol/conc. ammonia=6/3.5/0.5/0.05. The crude product is digested with diethyl ether. 1.06 g (50%) of the title compound are obtained as a crystalline solid. M.p. 114–117° C.

17. (5-Chloro-2,6-dimethylpyrimidin-4-yl)-[3-methyl-4-(4-piperazin-1-ylbutylsulfanyl)pyridin-2-ylmethyl]amine 5 g (12.97 mmol) of [4-(4-chlorobutylsulfanyl)-3-methylpyridin-2-ylmethyl]-(5-chloro-2,6-dimethylpyrimidin-4-yl)amine are refluxed in 100 ml of acetonitrile for 18 hours together with 6.84 g (77.84 mmol) of piperazine, 4.12 g (38.91 mmol) of sodium carbonate and a catalytic amount of sodium iodide. Acetonitrile is stripped off in vacuo and the residue is taken up in 100 ml of water. It is extracted five times with 30 ml of chloroform/methanol=10/1 each time. The combined organic phases are washed with water and concentrated. The residue is chromatographed on silica gel using chloroform/methanol/triethylamine=10/2/0.1. The crude product is digested with diethyl ether. 3.81 g (68%) of the title compound are obtained as a crystalline solid. M.p. 143–145° C.

18. (5-Chloro-2,6-dimethylpyrimidin-4-yl)-[3-chloro-4-(methyl-{3-[2-(2-methyl-5nitroimidazol-1-yl)ethylsulfanyl]propyl}amino)pyridin-2-ylmethyl]amine 0.5 ml (3.0 mmol) of 6 N sodium hydroxide solution is added dropwise under a nitrogen atmosphere in the course of 0.5 h to a suspension of 0.39 g (1.0 mmol) of {3-chloro-4-[(3-chloropropyl)methylamino]pyridin-2-ylmethyl}-(5-chloro-2,6-dimethylpyrimidin-4-yl)amine and 0.5 g (1.8 mmol) of 2-[2-(2-methyl-5-nitroimidazol-1-yl)ethyl]isothiourea hydrochloride in ethanol (20 ml). The suspension is stirred at 60° C. for 1 h and then concentrated. The residue is taken up in 70 ml of water and 50 ml of ethyl acetate. The aqueous phase is extracted with 3×30 ml of ethyl acetate. The organic extracts are washed with 20 ml of water, dried over magnesium sulfate and concentrated. The residue is purified by chromatography on silica gel (eluent: toluene/dioxane=2:1). The fractions of $R_f$=0.22 are concentrated. 0.3 g (49%) of the title compound is obtained as a colorless solid. M.p. 123° C.–126° C.

19. (5-Chloro-2,6-dimethylpyrimidin-4-yl)-(3-methyl-4-{4-[2-(2-methyl-5-nitroimidazol-1-yl)-ethylsulfanyl]butylsulfanyl}pyridin-2-ylmethyl)amine 1.0 g (2.32 mmol) of [4-(4-bromobutylsulfanyl)-3-methylpyridin-2-ylmethyl]-(5-chloro-2,6-dimethylpyrimidin-4-yl)amine and 0.92 g (3.48 mmol) of 2-[2-(2-methyl-5-nitroimidazol-1-yl)ethyl]isothiuronium chloride are suspended in 20 ml of ethanol. 1.54 ml (9.24 mmol) of 6 N aqueous NaOH are added dropwise in the course of 30 minutes. The mixture is stirred at room temperature for 30 minutes and then heated at 60° C. for three hours. After cooling, it is diluted with 80 ml of water and extracted three times using 30 ml of ethyl acetate each time. The combined organic phases are concentrated. The residue is chromatographed on silica gel using toluene/ethyl acetate/methanol/conc. ammonia=6/3.6/0.4/0.05. The crude product is digested with diethyl ether. 0.56 g (45%) of the title compound is obtained as a crystalline solid. M.p. 142–144° C.

20. (5-Chloro-2,6-dimethylpyrimidin-4-yl)-{3-methyl-4-[4-(pyridin-4-ylmethylsulfanyl)butylsulfanyl]pyridin-2-ylmethyl}amine 1.0 g (2.32 mmol) of [4-(4-bromobutylsulfanyl)-3-methylpyridin-2-ylmethyl]-(5-chloro-2,6-dimethylpyrimidin-4-yl)amine and 0.84 g (3.49 mmol) of 2-pyridin-4-ylmethylisothiuronium chloride are suspended in 20 ml of ethanol. 1.54 ml (9.24 mmol) of 6 N aqueous NaOH are added dropwise in the course of 30 minutes. The mixture is stirred at room temperature for 30 minutes and then heated at 60° C. for 3 hours. After cooling, it is diluted with 80 ml of water and extracted three times using 25 ml of dichloromethane each time. The combined organic phases are concentrated. The residue is chromatographed on silica gel using toluene/ethyl acetate/methanol/conc. ammonia=6/35/0.5/0.05 The crude product is digested with diethyl ether. 1.09 g (99%) of the title compound are obtained as a crystalline solid. M.p. 104–106° C.

21. 5-(3-{2-[(5-Chloro-2,6-dimethylpyrimidin-4-ylamino)methyl]-3-methylpyridin-4-ylsulfanyl}propylsulfanylmethyl)-3-(4-methoxyphenyl)-oxazolidin-2-one hemifumarate 0.21 g (1.3 mmol) of 4-amino-5-chloro-2,6-dimethylpyrimidine is dissolved in 10 ml of dimethylformamide under a nitrogen atmosphere and 0.05 g of sodium hydride (80% strength suspension) is added in portions with vigorous stirring. The suspension is then stirred at room temperature for 1 h. A solution of 0.59 g (1.3 mmol) of 5-[3-(2-chloromethyl-3-methylpyridin-4-ylsulfanyl)propylsulfanylmethyl]-3-(4-methoxyphenyl)oxazolidin-2-one in dimethylformamide (10 ml) is then added dropwise in the course of 0.5 h and the mixture is stirred overnight at room temperature. The mixture is cooled to 0° C. and treated cautiously with water (50 ml) with vigorous stirring. It is then extracted with 3×50 ml of ethyl acetate. The organic extracts are washed with 50 ml of water, dried over magnesium sulfate and concentrated. The residue is purified by chromatography on silica gel (eluent: ethyl acetate). The oily residue obtained is dissolved in 10 ml of hot methanol and a solution of 0.14 g (1.2 mmol) of fumaric acid in 5 ml of methanol is added dropwise. After filtration and drying of the precipitate, 0.49 g (56%) of the title compound is obtained. M.p. 161°–164° C.

22. (5-Chloro-2,6-dimethylpyrimidin-4-yl)-{3-methyl-4-[3-(1-methylpiperidin-3-ylmethylsulfanyl)propylsulfanyl]pyridin-2-ylmethyl}amine 5 g (14 mmol) of 2-chloromethyl-3-methyl-4-[3(1-methylpiperidin-3-ylmethylsulfanyl)propylsulfanyl]pyridine hydrochloride are dissolved in about 50 ml of dichloromethane and the free base is liberated using saturated aqueous sodium hydrogencarbonate solution. The organic phase is separated off and concentrated. The residue is taken up in 75 ml of acetonitrile and treated with 2.43 g (15.4 mmol) of 4-amino-5-chloro-2,6-dimethylpyrimidine. The mixture is refluxed for 20 hours. Acetonitrile is stripped off in vacuo and the residue is taken up in 250 ml of water. The pH is adjusted to 8 using saturated sodium carbonate solution. The mixture is extracted four times using 50 ml of ethyl acetate each time. The combined organic phases are. concentrated. The residue is chromatographed on silica gel using isopropyl acetate/methanol/conc. ammonia=6/1/0.1. The crude product is then digested with diethyl ether. 2.62 g (40%) of the title compound are obtained as a crystalline solid. M.p. 92–94° C.

23. (5-Chloro-2,6-dimethylpyrimidin-4-yl)-{3-methyl-4-[3-(4-pyridin-4-ylmethylpiperazin-1-yl)propylsulfanyl]pyridin-2-ylmethyl}amine hydrochloride 1 g (2.37 mmol) of (5-chloro-2,6-dimethylpyrimidin-4-yl)-[3-methyl-4-(3-piperazin-1-yl-propylsulfanyl)pyridin-2-ylmethyl]amine is refluxed in 60 ml of acetone for 20 hours together with 0.4 g (2.37 mmol) of 4-chloromethylpyridine hydrochloride, 0.75 g (7.11 mmol) of sodium carbonate and a catalytic amount of sodium iodide. Acetone is stripped off in vacuo and the residue is taken up in 100 ml of water. It is extracted three times using 25 ml of dichloromethane each time. The combined organic phases are concentrated. The residue is chromatographed on silica gel using ethyl acetate/methanol=10/1. The crude product is digested with diethyl ether. 1.33 g (73%) of the title compound are obtained as a crystalline solid. M.p. 166–168° C.

24. (5-Chloro-2,6-dimethylpyrimidin-4-yl)-{3-methyl-4-[3-(pyridin-4-ylmethylsulfanyl)propylsulfanyl]pyridin-2-ylmethyl}amine 1.5 g (4.04 mmol) of [4-(3-chloropropylsulfanyl)-3-methylpyridin-2-ylmethyl]-(5-chloro-2,6-dimethylpyrimidin-4-yl)amine and 2.0 g (8.4 mmol) of 2-pyridin-4-ylmethylisothiuronium chloride are suspended in 30 ml of ethanol. 2 ml (12 mmol) of 6 N aqueous NaOH are added dropwise in the course of 30 minutes. The mixture is stirred at room temperature for 30 minutes and heated at 60° C. for 3 hours. After cooling, it is diluted with 100 ml of water and extracted three times using 30 ml of ethyl acetate each time. The combined organic phases are concentrated. The residue is chromatographed on silica gel using ethyl acetate/methanol/conc. ammonia=15/1/0.1. The crude product is digested with diethyl ether. 1.48 g (80%) of the title compound are obtained as a crystalline solid. M.p. 124–125° C.

25. (5-Chloro-2,6-dimethylpyrimidin-4-yl)-[3-methyl-4-(3-(piperazin-1-ylpropylsulfanyl)-pyridin-2-ylmethyl]amine 2 g (5.38 mmol) of (4-(3-chloropropylsulfanyl)-3-methylpyridin-2-ylmethyl]-(5-chloro-2,6-dimethylpyrimidin-4-yl)amine are refluxed in 40 ml of acetonitrile for 20 hours together with 0.36 g (4.04 mmol) of piperazine, 1.71 g (16.14 mmol) of sodium carbonate and 0.08 g (0.54 mmol) of sodium iodide. Acetonitrile is stripped off in vacuo and the residue is taken up in 150 ml of water and the pH is adjusted to 8 using 2 M acetic acid. The mixture is extracted four times using 25 ml of chloroform/methanol=10/1 each time. The combined organic phases are concentrated. The residue is chromatographed on silica gel using chloroform/methanol/triethylamine=10/1/0.1. The crude product is digested with diethyl ether. 0.24 g (12%) of the title compound is obtained as a crystalline solid. M.p.: 144–145° C.

26. 1,4-bis{3-[(3-Methyl-4-ylsulfanylpyridin-2-ylmethyl)-5-chloro-2,6-dimethylpyrimidin-4-ylamino]propyl}piperazine 2 g (5.38 mmol) of [4-(3-chloropropylsulfanyl)-3-methylpyridin-2-ylmethyl]-(5-chloro-2,6-dimethylpyrimidin-4-yl)amine are refluxed in 40 ml of acetonitrile for 20 hours together with 0.36 g (4.04 mmol) of piperazine, 1.71 g (16.14 mmol) of sodium carbonate and 0.08 g (0.54 mmol) of sodium iodide. Acetonitrile is stripped off in vacuo and the residue is taken up in 150 ml of water and the pH is adjusted to 8 using 2 M acetic acid. The mixture is extracted four times using 25 ml of chloroform/methanol=10/1 each time. The combined organic phases are concentrated. The residue is chromatographed on silica gel using chloroform/methanol/triethylamine=10/1/0.1. The crude product is digested with acetonitrile. 0.63 g (31%) of the title compound is obtained as a crystalline solid. M.p.: 234–237° C.

27. (5-Chloro-2,6-dimethylpyrimidin-4-yl)-(3-methyl-4-{3-[2-(2-methyl-5-nitroimidazol-1-yl)-ethylsulfanyl]propylsulfanyl}pyridin-2-ylmethyl)amine 1 g (2.69 mmol) of [4-(3-chloropropylsulfanyl)-3-methylpyridin-2-ylmethyl]-(5-chloro-2,6-dimethylpyrimidin-4-yl)amine and 1.72 g (6.47 mmol) of 2-[2-(2-methyl-5-nitroimidazol-1-yl)-ethyl]isothiuronium chloride are suspended in 20 ml of ethanol. 1.73 ml (10.38 mmol) of 6 N aqueous NaOH are added dropwise in the course of 20 minutes. The mixture is stirred at room temperature for 30 minutes and then heated at 60*C. for three hours. After cooling, it is diluted with 50 ml of water and extracted three times using 25 ml of dichloromethane each time. The combined organic phases are concentrated. The residue is chromatographed on silica gel using toluene/ethyl acetate/methanol/conc. ammonia=6/3/1/0.1. The crude product is digested with diethyl ether. 0.97 g (69%) of the title compound is obtained as a crystalline solid. M.p.: 145–147° C.

28. (5-Chloro-2,6-dimethyl-pyrimidin-4-yl)-[3-methyl-4-(2-{2-[2-(2-methyl-5nitro-imidazol-1-yl)ethylsulfanyl]-ethoxy}-ethoxy)-pyridin-2-ylmethyl]-amine (5-Chloro-2,6-dimethyl-pyrimidin-4-yl)-{4-[2-(2-chloro-ethoxy)-ethoxy]-3-methyl-pyridin-2-ylmethyl}-amine (1.2 g, 3.11 mmol) and 2-[2-(2-methyl-5-nitro-imidazol-1-yl)-ethyl]-isothiourea-hydrochloride (1.84 g, 6.92 mmol) are suspended in 25 ml of ethanol under an atmosphere of nitrogen. 6 N NaOH (1.6 ml, 9.6 mmol) is added during 30 minutes. The suspension is stirred for 30 minutes at room temperature and then for 6 hours at 60° C. The mixture is poured on 150 ml of water and extracted three times with 50 ml of dichloromethane. The combined organic phases are concentrated in vacuo. The residue is purified by chromatography over silica with toluene/ethyl acetate/methanol/conc. ammonia=6/3.5/0.5/0.05. The crude product is triturated with diethyletherYield: 0.39 g, 23%), Mp.; 102–105° C.

29. (5-Chloro-2,6-dimethyl-pyrimidin-4-yl)-(3-methyl-4-{2-[2-(pyridin-4-ylmethylsulfanyl)-ethoxy]-ethoxy}-pyridin-2-ylmethyl)-amine The compound is obtained analogously to Example 28 from (5-chloro-2,6-dimethyl-pyrimidin-4-yl)-{4-[2-(2-chloro-ethoxy)-ethoxy]-3-methyl-pyridin-2-ylmethyl}-amine (1.2 g, 3.11 mmol) and 2-pyridin-4-ylmethyl-isothiourea-dihydrochloride (1.05 g, 4.37 mmol). Yield: 1.13 g (77%). Mp.: 103–105° C.

30. (5-Chloro-2,6-dimethyl-pyrimidin-4-yl)-{3-methyl-4-[2-(pyridin-4-ylmethylsulfanyl)-ethoxy]-pyridin-2-ylmethyl}-amine The compound is obtained analogously to Example 28 from (5-chloro-2,6-dimethyl-pyrimidin-4-yl)-[4-(2-chloro-ethoxy)-3-methyl-pyridin-2-ylmethyl]-amine (1.5 g, 4.39 mmol) and 2-pyridin-4-ylmethyl-isothiourea-dihydrochloride (1.26 g, 5.25 mmol). Yield: 1.56 g (83%). Mp.: 140–142° C.

31. 2-(3-{2-[(5-Chloro-2,6-dimethyl-pyrimidin-4-ylamino)-methyl]-3-methyl-pyridin-4-ylsulfanyl}-propylsulfanyl)-ethanol (5-Chloro-2,6-dimethyl-pyrimidin-4-yl)-[4-(3-chloro-propylsulfanyl)-3-methyl-pyridin-2-ylmethyl]-amine (1.5 g, 4.03 mmol) and 2-mercaptoethanol (0.5 g, 6.41 mmol) are suspended in 30 ml of ethanol under an atmosphere of nitrogen. 6 N NaOH (2 ml, 12 mmol) is added. The mixture is stirred for 2 hours at 60° C. The mixture is poured on 150 ml of water and extracted three times with 50 ml of dichloromethane. The combined organic phases are concentrated in vacuo. The crystalline crude product is triturated with diethyl etherYield: 1.5 g, 90%). Mp.: 134–137° C.

32. (5-Chloro-2,6-dimethyl-pyrimidin-4-yl)-(3-methyl-4-{2-[2-(2-methyl-5-nitro-imidazol-1-yl)-ethylsulfanyl]-ethoxy}-pyridin-2-ylmethyl)-amine The compound is obtained analogously to Example 28 from (5-chloro-2,6-dimethyl-pyrimidin-4-yl)-[4-(2-chloro-ethoxy)-3-methyl-pyridin-2-ylmethyl)-amine (1.5 g, 4.39 mmol) and 2-[2-(2-methyl-5-nitro-imidazol-1-yl)-ethyl]-isothiourea-hydrochloride (3.23 g, 12.16 mmol). Yield: 0.99 g (46%). Mp.: 139–144° C.

33. (5-Chloro-2,6-dimethyl-pyrimidin-4-yl)-(3-methyl-4-{3-[2-(2-methyl-5-nitro-imidazol-1-yl)-ethylsulfanyl]-propoxy}-pyridin-2-ylmethyl)-amine The compound is obtained analogously to Example 28 from (5-chloro-2,6-dimethyl-pyrimidin-4-yl)-[4-(3-chloropropoxy)-3-methyl-pyridin-2-ylmethyl]-amine (1.3 g, 3.65 mmol) and 2-[2-(2-methyl-5-nitro-imidazol-1-yl)-ethyl]-isothiourea-hydrochloride (1.94 g, 7.31 mmol). Yield: 1.23 g (67%). Mp.: 169–171° C.

34. (5-Chloro-2,6-dimethyl-pyrimidin-4-yl)-{3-methyl-4-[3-(pyridin-4-ylmethylsulfanyl)-propoxy]-pyridin-2-ylmethyl}-amine The compound is obtained analogously to Example 28 from (5-chloro-2,6-dimethyl-pyrimidin-4-yl)-[4-(3-chloro-propoxy)-3-methyl-pyridin-2-ylmethyl]-amine (1.3 g, 3.65 mmol) and 2-pyridin-4-ylmethyl-isothiourea-dihydrochloride (1.32 g, 5.48 mmol). Yield: 1.19 g (73%). Mp.: 111–113° C.

35. 2-[2-(2-{2-[(5-Chloro-2,6-dimethyl-pyrimidin-4-ylamino)-methyl]-3-methyl-pyridin-4-yloxy}-ethoxy)-ethylsulfanyl]-ethanol The compound is obtained analogously to Example 31 from (5-chloro-2,6-dimethyl-pyrimidin-4-yl)-{4-[2-(2-chloro-ethoxy)-ethoxy]-3-methyl-pyridin-2-ylmethyl}-amine (1.0 g, 2.59 mmol) and 2-mercaptoethanol (0.32 g, 4.10 mmol). Yield: 0.89 g (80%). Mp.: 114–116° C.

36. 2-(4-{2-[(5-Chloro-2,6-dimethyl-pyrimidin-4-ylamino)-methyl]-3-methyl-pyridin-4-yloxy}-butylsulfanyl)-ethanol The compound is obtained analogously to Example 31 from [4-(4-chloro-butoxy)-3-methyl-pyridin-2-ylmethyl]-(5-chloro-2,6-dimethyl-pyrimidin-4-yl)-amine (1.5 g, 4.06 mmol) and 2-mercaptoethanol (0.50 g, 6.41 mmol). Yield: 1.37 g (82%). Mp.: 116–118° C.

37. 2-(4-{2-[(5-Chloro-2,6-dimethyl-pyrimidin-4-ylamino)-methyl]-3-methyl-pyridin-4-ylsulfanyl}-butylsulfanyl)-ethanol The compound is obtained analogously to Example 31 from [4-(4-chloro-butylsulfanyl)-3-methyl-pyridin-2-ylmethyl]-(5-chloro-2,6-dimethyl-pyrimidin-4-yl)-amine (1.5 g, 3.89 mmol) and 2-mercaptoethanol (0.48 g, 6.15 mmol). Yield: 1.29 g (78%). Mp.; 142–143° C.

38. 5-[4-(3-{2-[(5-Chloro-2,6-dimethyl-pyrimidin-4-ylamino)-methyl]-3-methyl-pyridin-4-ylsulfanyl}-propyl)-piperazin-1-ylmethyl]-3-pyridin-4-ylmethyl-oxazolidin-2-one (5-Chloro-2,6-dimethyl-pyrimidin-4-yl)-[4-(3-chloro-propylsulfanyl)-3-methyl-pyridin-2-ylmethyl]-amine (1.5 g, 4.03 mmol) and 5-piperazin-1-ylmethyl-3-pyridin-4-ylmethyl-oxazolidin-2-one (2.23 g, 8.04 mmol) are refluxed in 30 ml of acetonitril for 12 hours together with $K_2CO_3$ (1.1 g, 8.08 mmol) and a catalytic amount of sodium iodide. The mixture is poured on 150 ml of water and extracted four times with 25 ml of dichloromethane. The combined organic phases are concentrated in vacuo. The residue is purified by chromatography over silica with toluene/ethyl acetate/methanol/conc. ammonia=6/3/1/0.05. The crude product is triturated with diethyl ether. Yield: 0.46 g (19%). Mp.: 123–126° C.

39. 2-(3-{2-[(5-Chloro-2,6-dimethyl-pyrimidin-4-ylamino)-methyl]-3-methyl-pyridin-4-ylsulfanyl}-propylsulfanyl)-β-D-glucopyranoside (5-Chloro-2,6-dimethyl-pyrimidin-4-yl)-[4-(3-chloro-propylsulfanyl)-3-methyl-pyridin-2-ylmethyl]-amine (1.5 g, 4.03 mmol) and 1-thio-β-D-glucose-sodium salt (0.88 g, 4.04 mmol) are suspended in 30 ml of isopropanol for 10 hours. The mixture is poured on 150 ml of water and extracted three times with 50 ml of dichloromethane. The resulting suspension is extracted with 50 ml chloroform/methanol=9/1. The combined organic phases are concentrated in vacuo. The residue is purified by chromatography over silica with dichloromethane/methanol=9/1. The crude product is triturated with diethyl ether. Yield: 1.03 g (48%). Mp.: 168–172° C.

40. (5-Chloro-2,6-dimethyl-pyrimidin-4-yl)-{3-methyl-4-[3-(3-nitro-thiophen-2-ylsulfanyl)-propylsulfanyl]-pyridin-2-ylmethyl}-amine Sodium hydride (0.14 g, 6.00 mmol) is suspended in 5 ml of DMF. A solution of 4-amino-5-chloro-2,6-dimethylpyrimidine (1.32 g, 8.2 mmol) in 15 ml of DMF is added slowly. The solution is stirred for one hour. (2-Chloromethyl-3-methyl-4-[3-(3-nitro-thiophen-2-ylsulfanyl)-propylsulfanyl]-pyridine-hydrochloride (2.25 g, 5.47 mmol) is suspended in 20 ml of water. A solution of $NaHCO_3$ in water (20 ml) is added. The mixture is extracted with 20 ml of dichloromethane. The organic phase is dried over $MgSO_4$ and concentrated in vacuo. The residue is dissolved in 5 ml of DMF and added slowly to the above prepared solution of 4-amino-5-chloro-2,6-dimethylpyrimidine sodium salt. The mixture is stirred for 18 hours at room temperature and afterwards concentrated in vacuo. The residue is suspended in 100 ml of water and extracted four times with 25 ml of dichloromethane. The combined organic phases are concentrated in vacuo. The residue is purified by chromatography over silica with toluene/ethyl acetate/methanol/conc. ammonia=6/3.6/0.4/0.05. The crude product is triturated with diethyl ether. Yield: 1.52 g (56%). Mp.: 174–180° C.

41. (5-Chloro-2,6-dimethyl-pyrimidin-4-yl)-(3-methyl-4-{3-[2-(pyrimidin-2-ylsulfanyl)-ethylsulfanyl]-propylsulfanyl}-pyridin-2-ylmethyl)-amine (5-Chloro-2,6-dimethyl-pyrimidin-4-yl)-{4-[3-(2-chloro-ethylsulfanyl)-propylsulfanyl]-3-methyl-pyridin-2-ylmethyl}-amine-hydrochloride (1.5 g, 3.20 mmol) and 2-mercaptopyrimidine (0.39 g, 3.37 mmol) and $Na_2CO_3$ (1.0 g, 9.6 mmol) are refluxed in 30 ml of acetonitril for 12 hours. The mixture is concentrated in vacuo. The residue is suspended in 100 ml of water and extracted four times with 25 ml of dichloromethane. The combined organic phases are concentrated in vacuo. The residue is purified by chromatography over silica with toluene/ethyl acetate/methanol=6/3.5/0.5. The crude product is triturated with diethyl ether. Yield: 0.92 g (57%). Mp.: 112–115° C.

42. (5-Chloro-2,6-dimethyl-pyrimidin-4-yl)-(3-methyl-4-{2-[2-(pyridin-4-ylmethylsulfanyl)-ethoxy]-ethylsulfanyl}-pyridin-2-ylmethyl)-amine The compound is obtained analogously to Example 28 from (5-chloro-2,6-dimethyl-pyrimidin-4-yl)-{4-[2-(2-chloro-ethoxy)-ethylsulfanyl]-3-methyl-pyridin-2-ylmethyl}-amine (1.5 g, 3.73 mmol) and 2-pyridin-4-ylmethyl-isothiourea-dihydrochloride (1.35 g, 5.62 mmol). Yield: 1.34 g (74%). Mp.: 68–71° C.

43. (5-Chloro-2,6-dimethyl-pyrimidin-4-yl)-[3-methyl-4-(2-{2-[2-(pyridin-4-ylmethylsulfanyl)-ethoxy]-ethoxy}-ethylsulfanyl)-pyridin-2-ylmethyl]-amine The compound is obtained analogously to Example 28 from (5-chloro-2,6-dimethyl-pyrimidin-4-yl)-(4-{2-[2-(2- chloro-ethoxy)-ethoxy]-ethylsulfanyl}-3-methyl-pyridin-2-ylmethyl)-amine (2.0 g, 4.49 mmol) and 2-pyridin-4-ylmethyl-isothiourea-dihydrochloride (1.62 g, 6.73 mmol). Yield: 1.50 g (63%). Mp.: 84–86° C.

44. (5-Chloro-2,6-dimethyl-pyrimidin-4-yl)-[3-methyl-4-(1-methyl-piperidin-3-ylmethylsulfanyl)-pyridin-2-ylmethyl]-amine The compound is obtained analogously to Example 40 from 4-amino-5-chloro-2,6-dimethylpyrimidine (1.55 g, 9.63 mmol) and 2-chloromethyl-3-methyl-4-(1-methyl-piperidin-3-ylmethylsulfanyl)-pyridine-hydrochloride (3.0 g, 9.63 mmol). The coupling reaction is carried out at 0° C. (two hours reaction time). The chromatography is done with toluene/ethyl acetate/methanol/conc. ammonia=6/3.5/0.5/0.05. The crude product is triturated with diethyl ether. Yield: 2.23 g (57%). Mp.: 148–149° C.

45. (5-Chloro-pyrimidin-4-yl)-{3-methyl-4-[3-(4-pyridin-4-ylmethyl-piperazin-1-yl)-propylsulfanyl]-pyridin-2-ylmethyl}-amine (5-Chloro-pyrimidin-4-yl)-[3-methyl-4-(3-piperazin-1-yl-propylsulfanyl)-pyridin-2-ylmethyl]-amine (1.0 g, 2.54 mmol) and 4-picolylchloride-hydrochloride (0.57 g, 3.51 mmol) are refluxed in 25 ml of acetone for 8 hours together with Na$_2$CO$_3$ (1 g, 9.43 mmol) and a catalytic amount of sodium iodide. The mixture is concentrated in vacuo. The residue is suspended in 150 ml of water and extracted four times with 25 ml of dichloromethane. The combined organic phases are concentrated in vacuo. The residue is purified by chromatography over silica with dichloromethane/methanol/triethylamine=10/1/0.1. The crude product is triturated with diethyl ether. Yield: 0.74 g (60%). Mp.: 149–151° C.

46. (5-Chloro-2,6-dimethyl-pyrimidin-4-yl)-[3-methyl-4-(pyridin-4-ylmethylsulfanyl)-pyridin-2-ylmethyl]-amine (5-Chloro-2,6-dimethyl-pyrimidin-4-yl)-(4-chloro-3-methyl-pyridin-2-ylmethyl)-amine (1.0 g, 3.36 mmol) and 2-pyridin-4-ylmethyl-isothiourea-dihydrochloride (1.21 g, 5.04 mmol) and K$_2$CO$_3$ (1.4 g, 10.06 mmol) are stirred at 80° C. in 15 ml of DMF for three days. The mixture is poured on 100 ml of water and extracted three times with 25 ml of dichloromethane. The combined organic phases are concentrated in vacuo. The residue is purified by chromatography over silica with toluene/ethyl acetate/methanol/conc. ammonia=6/3.5/0.5/0.01. The crude product is triturated with diethyl ether. Yield: 0.46 g, 36%). Mp.: 188–1.90° C.

47. (5-Chloro-2,6-dimethyl-pyrimidin-4-yl)-{3-methyl-4-[3-(pyridin-3-ylmethylsulfanyl)-propylsulfanyl]-pyridin-2-ylmethyl}-amine The compound is obtained analogously to Example 28 from (5-chloro-2,6-dimethyl-pyrimidin-4-yl)-[4-(3-chloro-propylsulfanyl)-3-methyl-pyridin-2-ylmethyl]-amine (1.5 g, 4.04 mmol) and 2-pyridin-3-ylmethyl-isothiourea-dihydrochloride (1.46 g, 6.08 mmol). Yield: 1.48 g (80%). Mp.: 104–105° C.

48. (5-Chloro-2,6-dimethyl-pyrimidin-4-yl)-{3-methyl-4-[3-(pyridin-2-ylmethylsulfanyl)-propylsulfanyl]-pyridin-2-ylmethyl}-amine The compound is obtained analogously to Example 28 from (5-chloro-2,6-dimethyl-pyrimidin-4-yl)-[4-(3-chloro-propylsulfanyl)-3-methyl-pyridin-2-ylmethyl]-amine (1.5 g, 4.04 mmol) and 2-pyridin-2-ylmethyl-isothiourea-dihydrochloride (1.46 g 6.08 mmol). Yield: 1.57 g (85%). Mp.: 100–101° C.

49. (5-Chloro-pyrimidin-4-yl)-(3-methyl-4-{2-[2-(2-methyl-5-nitro-imidazol-1-yl)-ethylsulfanyl]-ethoxy}-pyridin-2-ylmethyl)-amine The compound is obtained analogously to Example 28 from [4-(2-chloro-ethoxy)-3-methyl-pyridin-2-ylmethyl]-(5-chloro-pyrimidin-4-yl)-amine (1.5 g, 4.78 mmol) and 2-[2-(2-methyl-5-nitro-imidazol-1-yl)-ethyl]-isothiourea-hydrochloride (1.90 g, 7.18 mmol). Yield: 0.45 g (20%). Mp.: 145–147° C.

50. (5-Chloro-2,6-dimethyl-pyrimidin-4-yl)-{3-methyl-4-14-(pyridin-3-ylmethylsulfanyl)-butoxy]-pyridin-2-ylmethyl}-amine The compound is obtained analogously to Example 28 from [4-(4-chloro-butoxy)-3-methyl-pyridin-2-ylmethyl]-(5-chloro-2,6-dimethyl-pyrimidin-4-yl)-amine (1.5 g, 4.06 mmol) and 2-pyridin-3-ylmethyl-isothiourea-dihydrochloride (1.46 g, 6.08 mmol). Yield: 1.38 g (74%). Mp.: 94–95° C.

51. (5-Chloro-2,6-dimethyl-pyrimidin-4-yl)-{3-methyl-4-[4-(pyridin-2-ylmethylsulfanyl)-butoxy]-pyridin-2-ylmethyl}-amine The compound is obtained analogously to Example 28 from [4-(4-chloro-butoxy)-3-methyl-pyridin-2-ylmethyl]-(5chloro-2,6-dimethyl-pyrimidin-4-yl)-amine (1.5 g, 4.06 mmol) and 2-pyridin-2-ylmethyl-isothiourea-dihydrochloride (1.46 g, 6.08 mmol). Yield: 1.63 g (88%). Mp.: 113–114° C.

52. (5-Chloro-2,6-dimethyl-pyrimidin-4-yl)-(3-methyl-4-{2-[2-(pyridin-3-ylmethylsulfanyl)-ethoxy]-ethylsulfanyl}-pyridin-2-ylmethyl)-amine The compound is obtained analogously to Example 28 from (5-chloro-2,6-dimethyl-pyrimidin-4-yl)-{4-[2-(2-chloro-ethoxy)-ethylsulfanyl]-3-methyl-pyridin-2-ylmethyl}-amine (2.0 g, 4.98 mmol) and 2-pyridin-3-ylmethyl-isothiourea-dihydrochloride (1.79 g, 7.46 mmol). Yield: 1.75 g (72%). Mp.: 90–92° C.

53. (5-Chloro-2,6-dimethyl-pyrimidin-4-yl)-(3-methyl-4-{2-[2-(pyridin-2-ylmethylsulfanyl)-ethoxy]ethylsulfanyl}-pyridin-2-ylmethyl)-amine The compound is obtained analogously to Example 28 from (5-chloro-2,6-dimethyl-pyrimidin-4-yl)-{4-[2-(2-chloro-ethoxy)-ethylsulfanyl]-3-methyl-pyridin-2-ylmethyl}-amine (2.0 g, 4.98 mmol) and 2-pyridin-2-ylmethyl-isothiourea-dihydrochloride (1.79 g, 7.46 mmol). Yield: 2.07 g (85%). Mp.: 70–72° C.

54. (5-Chloro-pyrimidin-4-yl)-{3-methyl-4-[2-(pyridin-4-ylmethylsulfanyl)-ethoxy)-pyridine-2-ylmethyl}-amine The compound is obtained analogously to Example 28 from (4-(2-chloro-ethoxy)-3-methyl-pyridin-2-ylmethyl]-(5-chloro-pyrimidin-4-yl)-amine (1.3 g, 4.15 mmol) and 2-pyridin-4-ylmethyl-isothiourea-dihydrochloride (1.50 g, 6.25 mmol). Yield: 1.3 g (78%). Mp.: 119–121° C.

55. 2-({3-Chloro-2-[(5-chloro-pyrimidin-4-ylamino)-methyl]-pyridin-4-yl}-methyl-amino)-ethanol The compound is obtained analogously to Example 2 from 2-[(3-chloro-2-chloromethyl-pyridin-4-yl)-methylamino]-ethanol (4.7 g, 20 mmol) and 4-amino-5-chloro-pyrimidin (2.6 g, 20 mmol). Yield: 2.64 g (29%). Mp.: 158–161° C.

56. (5-Chloro-pyrimidin-4-yl)-(3-methyl-4-{3-[2-(2-methyl-5-nitro-imidazol-1-yl)-ethylsulfanyl]-propoxy}-pyridin-2-ylmethyl)-amine The compound is obtained analogously to Example 28 from (5-chloro-pyrimidin-4-yl)-[4-(3-chloro-propoxy)-3-methyl-pyridin-2-ylmethyl]-amine (2.0 g, 6.11 mmol) and 2-[2-(2-methyl-5-nitro-imidazol-1-yl)-ethyl]-isothiourea-hydrochloride (2.43 g, 9.17 mmol). Yield: 0.9 g (31%). Mp.: 143–146° C.

57. (5-Chloro-2,6-dimethyl-pyrimidin-4-yl)-(3-methyl-4-{2-[2-(2-methyl-5-nitro-imidazol-1-yl)-ethoxy]-ethylsulfanyl}-pyridin-2-ylmethyl)-amine (5-Chloro-2,6-dimethyl-pyrimidin-4-yl)-{4-[2-(2-chloro-ethoxy)-ethylsulfanyl]-3-methyl-pyridin-2-ylmethyl}-amine (2.0 g, 4.98 mmol), 2-methyl-5-nitro-imidazole (0.76 g, 5.98 mmol), $K_2CO_3$ (2.07 g, 14.94 mmol) and a catalytic amount of sodium iodide are suspended in 25 ml of acetonitril and stirred at 80° C. for 20 hours. The mixture is poured on 100 ml of water and extracted three times with 30 ml of dichloromethane. The combined organic phases are washed with water and concentrated in vacuo. The residue is purified by chromatography over silica with toluene/ethyl acetate/methanol/conc. ammonia=6/3/1/0.01. The crude product is triturated with diethyl ether. Yield: 0.19 g (8%). Mp.: 160–163° C.

58. (5-Chloro-pyrimidin-4-yl)-{4-[2-(furan-2-ylmethylsulfanyl)-ethoxy]-3-methyl-pyridin-2-ylmethyl}-amine Methanesulfonic acid 2-{2-[(5-chloro-pyrimidin-4-ylamino)-methyl]-3-methyl-pyridin-4-ylsulfanyl}-ethyl ester (1.5 g, 4.0 mmol) and furfurylmercaptane (0.7 g, 12 mmol) are dissolved in 15 ml of DMF. Lithium hydroxide (0.29 g, 12 mmol) in 1.5 ml of water is added. The mixture is stirred at 60° C. for one hour. The mixture is poured on 100 ml of water and extracted three times with 30 ml of dichloromethane. The combined organic phases are washed with water and concentrated in vacuo. The residue is purified by chromatography over silica with toluene/ethyl acetate/methanol/conc. ammonia=6/3.6/0.4/0.01. The crude product is triturated with diethyl ether. Yield: 1.11 g (71%). Mp.: 129–130° C.

59. (5-Chloro-pyrimidin-4-yl)-[4-(furan-2-ylmethylsulfanyl)-3-methyl-pyridin-2-ylmethyl]-amine The compound is obtained analogously to Example 40 from 4-amino-5-chloro-pyrimidine (1.34 g, 10.33 mmol) and 2-chloromethyl-4-(furan-2-ylmethylsulfanyl)-3-methyl-pyridine-hydrochloride (3.0 g, 10.33 mmol). The chromatography is done with toluene/ethyl acetate/methanol/conc. ammonia=6/3.5/0.5/0.01. The crude product is triturated with diethyl ether. Yield: 1.77 g (49%). Mp.: 169–170° C.

60. (5-Chloro-2,6-dimethyl-pyrimidin-4-yl)-[4-(furan-2-ylmethylsulfanyl)-3-methyl-pyridin-2-ylmethyl]-amine The compound is obtained analogously to Example 40 from 4-amino-5-chloro-2,6-dimethylpyrimidine (1.63 g, 10.33 mmol) and 2-chloromethyl-4-(furan-2-ylmethylsulfanyl)-3-methyl-pyridine-hydrochloride (3.0 g, 10.33 mmol). The chromatography is done with toluene/ethyl acetate/methanol/conc. ammonia=6/3.5/0.5/0.01. The crude product is triturated with diethyl ether. Yield: 2.17 g (56%). Mp.: 159–160° C.

Starting Compounds

A. [4-(3-Chloropropylsulfanyl)-3-methylpyridin-2-ylmethyl]-(5-Chloro2,6-dimethylpyrimidin-4-yl)amine 1.04 g (26.07 mmol) of sodium hydride (60% strength in paraffin) are introduced into 10 ml of dimethylformamide. 5.6 g (34.76 mmol) of 4-amino-5-chloro-2,6-dimethylpyrimidine in 30 ml of dimethylformamide are added dropwise. The mixture is stirred at room temperature for one hour. 5 g (17.38 mmol) of [4-(3-chloropropylsulfanyl)-2-chloromethyl-3-methylpyridine hydrochloride are then suspended in 100 ml of dichloromethane and the free base is liberated using saturated aqueous sodium hydrogencarbonate solution. The organic phase is dried over magnesium sulfate and concentrated. The residue is taken up in 10 ml of dimethylformamide and added dropwise to the previously prepared solution. The mixture is stirred at room temperature for 2 hours. Dimethylformamide is stripped off in a high vacuum and the residue is taken up in 150 ml of water. The solution is extracted four times with 30 ml of dichloromethane each time. The combined organic phases are washed with water, dried over magnesium sulfate and concentrated. The residue is chromatographed on silica gel using toluene/ethyl acetate/methanol/conc. ammonia=5/4/1/0.1. 3.49 g (540/.) of the title compound are obtained as a crystalline solid, which is used without further purification.

B. (5-Chloro-2,6-dimethylpyrimidin-4-yl)-[3-methyl-4-(3-piperazin-1-ylpropylsulfanyl)pyridin-2-ylmethyl]amine 3 g (8.08 mmol) of (5-chloro-2,6-dimethylpyrimidin-4-yl)-[4-(3-chloropropylsulfanyl)-3-methylpyridin-2-ylmethyl]amine are refluxed in 60 ml of acetonitrile for 20 hours together with 4.18 g (48.47 mmol) of piperazine, 2.57 g (24.24 mmol) of sodium carbonate and a catalytic amount of sodium iodide. Acetonitrile is stripped off in vacuo and the residue is taken up in 75 ml of water. The solution is extracted three times using 30 ml of chloroform/methanol=10/1 each time. The combined organic phases are washed with water, dried over magnesium sulfate and concentrated. The residue is chromatographed on silica gel using chloroform/methanol/triethylamine=10/210.1. The crude product is digested with diethyl ether. 2.74 g (81%) of the title compound are obtained as a crystalline solid. M.p.: 144–145° C.

C. 2-Chloromethyl-3-methyl-4-[3-(1-methylpiperidin-3-ylmethylsulfanyl)propylsulfanyl]-pyridine hydrochloride

C1. 2-Hydroxymethyl-3-methyl-4-[3-(1-methylpiperidin-3-ylmethylsulfanyl)propylsulfanyl]-pyridine hydrochloride 10 g (37.6 mmol) of [4-(3-mercaptopropylsulfanyl)-3-methylpyridin-2-yl]methanol hydrochloride and 6.58 g (35.73 mmol) of 3-chloromethyl-N-methylpiperidine hydrochloride are stirred in 70 ml of dimethylformamide at 50° C. for 5 hours together with 26 g (188 mmol) of potassium carbonate. Dimethylformamide is stripped off in a high vacuum. The mixture is diluted with 200 ml of water and extracted five times with 50 ml of ethyl acetate. The combined organic phases are washed with water, dried over magnesium sulfate and concentrated. The residue is chromatographed on silica gel using ethyl acetate/methanol/conc. ammonia=6/1/0.1. 8 g (63%) of the title compound are obtained as a yellow oil, which is used without further purification.

C2. 2-Chloromethyl-3-methyl-4-[3-(1-methylpiperidin-3-ylmethylsulfanyl)propylsulfanyl]-pyridine hydrochloride 3 g (8.83 mmol) of 2-hydroxymethyl-3-methyl-4-[3-(1-methylpiperidin-3-ylmethylsulfanyl)propylsulfanyl]-pyridine hydrochloride are dissolved in 50 ml of dichloromethane and treated with 1.26 g (10.6 mmol) of thionyl chloride in 10 ml of dichloromethane. The mixture is stirred at room temperature for 2 hours. It is then concentrated in vacuo and coevaporated twice with 30 ml of toluene each time. The residue is dried in vacuo. 3.5 g (100%) of the title compound are obtained as a green oil, which is used without further purification.

D. [4-(4-Bromobutylsulfanyl)-3-methylpyridin-2-ylmethyl]-(5-chloro-2,6-dimethylpyrimidin-4-yl) amine

D1. [4-(4-Bromobutylsulfanyl)-3-methylpyridin-2-yl]methanol 50 g (185 mmol) of 2-(2-hydroxymethyl-3-methylpyridin-4-yl)isothiuronium chloride are dissolved in a mixture of 270 ml of ethanol and 130 ml of water under a nitrogen atmosphere. 160 g (740 mmol) of 1,4-dibromobutane are added. 126.5 ml of a 6 N sodium hydroxide solution are added dropwise in the course of 45 minutes. The mixture is stirred at 50° C. for 24 hours. It is concentrated in vacuo and the residue is diluted with 400 ml of water. The mixture is extracted three times with 50 ml of dichloromethane each time. The combined organic phases are washed with water and concentrated. The residue is taken up again in 400 ml of water. The pH is adjusted to 8 using saturated aqueous sodium hydrogencarbonate solution. The mixture is extracted three times using 300 ml of toluene each time. The combined organic phases are washed with water, dried over magnesium sulfate and concentrated. The residue is chromatographed on silica gel using ethyl acetate/methanol/conc. ammonia=19/1/0.1. 11.67 g (22%) of the title compound are obtained as a yellow oil, which is used without further purification.

D2. 4-(4-Bromobutylsulfanyl)-2-chloromethyl-3-methylpyridine hydrochloride 11.5 g (39.62 mmol) of [4-(4-bromobutylsulfanyl)-3-methylpyridin-2-yl]methanol are dissolved in 75 ml of dichloromethane and treated with 7.07 g (59.43 mmol) of thionyl chloride in 20 ml of dichloromethane in the course of 20 minutes. The mixture is stirred at room temperature for 2 hours. It is concentrated in vacuo and coevaporated twice with 50 ml of toluene each time. The crude product is digested with diethyl ether. 11.97 g (88%) of the title compound are obtained as a crystalline solid, which is used without further purification.

D3. [4-(4-Bromobutylsulfanyl)-3-methylpyridin-2-ylmethyl]-(5-chloro-2,6-dimethylpyrimidin-4-yl) amine 0.76 g (19.1 mmol) of sodium hydride (60% strength in paraffin) is introduced into 5 ml of dimethylformamide. 4.2 g (26.07 mmol) of 4-amino-5-chloro-2,6-dimethylpyrimidine in 25 ml of dimethylformamide are added dropwise. The mixture is stirred at room temperature for one hour. 6 g (17.38 mmol) of 4-(4-bromobutylsulfanyl)-2-chloromethyl-3-methylpyridine hydrochloride are then suspended in 100 ml of dichloromethane and the free base is liberated using saturated aqueous sodium hydrogencarbonate solution. The organic phase is dried over magnesium sulfate and concentrated. The residue is taken up in 5 ml of dimethylformamide and added dropwise to the previously prepared solution. It is stirred at room temperature for 12 hours. Dimethylformamide is stripped off in a high vacuum and the residue is taken up in 150 ml of water. The solution is extracted twice with 50 ml of dichloromethane each time. The combined organic phases are washed with water, dried over magnesium sulfate and concentrated. The residue is chromatographed on silica gel using toluene/ethyl acetate/methanol/conc. ammonia=6/3.5/0.5/0.05. The crude product is digested with diethyl ether. 2.27 g (30%) of the title compound are obtained as a crystalline solid. M.p.: 127–128° C.

E. [4-(4-Chlorobutylsulfanyl)-3-methylpyridin-2-ylmethyl]-(5-chloro-2,6-dimethylpyrimidin-4-yl) amine

E1. 2-(2-Hydroxymethyl-3-methylpyridin-4-yl] isothiuronium chloride 40 g (206 mmol) of 4-chloro-2-hydroxymethyl-3-methylpyridine hydrochloride are refluxed in 400 ml of acetone for 14 hours together with 18.9 g (248 mmol) of thiourea. The mixture is then cooled to 0° C. and the precipitated solid is filtered off with suction. The solid is stirred in 200 ml of ethanol in the cold, filtered off with suction and dried in vacuo. 53.5 g (96%) of the title compound are obtained as a crystalline solid, which is used without further purification. M.p.: 142° C.

E2. 4-(2-Hydroxymethyl-3-methylpyridin-4-ylsulfanyl)butan-1-ol 50 g (185 mmol) of 2-(2-hydroxymethyl-3-methylpyridin-4-yl)isothiuronium chloride are dissolved in a mixture of 200 ml of ethanol and 100 ml of water under a nitrogen atmosphere. 83 g (740 mmol) of 4-chloro-1-butanol are added. 126.5 ml of a 6 N sodium hydroxide solution are added dropwise in the course of 45 minutes. The mixture is stirred at room temperature for 3 days. It is concentrated in vacuo and the residue is diluted with 500 ml of water. The mixture is extracted three times with 50 ml of dichloromethane each time. The combined organic phases are washed with water alnd concentrated. The residue is taken up again in 400 ml of water. The pH is adjusted to about 1 using HCl. The mixture is extracted twice with 50 ml of ethyl acetate each time in order to remove excess 4-chloro-1-butanol. The pH of the aqueous phase is adjusted to about 10 using NaOH. The mixture is extracted three times with 100 ml of dichloromethane each time. The combined organic phases are washed with water, dried over magnesium sulfate and concentrated. The residue is chromatographed on silica gel using toluene/dioxane/conc. ammonia=1/1/0.05. 21.8.g (52%) of the title compound are obtained as a crystalline solid. M.p.: 61–63° C.

E3. 4-(4-Chlorobutylsulfanyl)-2-chloromethyl-3-methylpyridine hydrochloride 15 g (49.9 mmol) of 4-(2-hydroxymethyl-3-methylpyridin-4-ylsulfanyl)butan-1-ol are dissolved in 200 ml of dichloromethane. 19.8 g (166.5 mmol) of thionyl chloride are slowly added dropwise. The mixture is stirred at room temperature for 24 hours. It is concentrated and coevaporated three times with 100 ml of toluene. The crystalline residue is digested with diethyl ether. 19.8 g (99%) of the title compound are obtained as a crystalline solid, which is used without further purification. M.p.: 154–157° C.

E4. [4-(4-Chlorobutylsulfanyl)-3-methylpyridin-2-ylmethyl]-(5-chloro-2,6-dimethylpyrimidin-4-yl)amine 2.2 g (54.87 mmol) of sodium hydride (60% strength in paraffin) are introduced into 10 ml of dimethylformamide. 12 g (74.83 mmol) of 4-amino-5-chloro-2,6-dimethylpyrimidine in 60 ml of dimethylformamide are added dropwise. The mixture is stirred at room temperature for one hour. 15 g (49.88 mmol) of 4-(4-chlorobutylsulfanyl)-2-chloromethyl-3-methylpyridine hydrochloride are then suspended in 100 ml of dichloromethane and the free base is liberated using saturated aqueous sodium hydrogencarbonate solution. The organic phase is dried over magnesium sulfate and concentrated. The residue is taken up in 15 ml of dimethylformamide and added dropwise to the previously prepared solution. The mixture is stirred at room temperature for 2 hours. Dimethylformamide is stripped off in a high vacuum and the residue is taken up in 350 ml of water. It is extracted twice with 50 ml of dichloromethane each time. The combined organic phases are washed with water, dried over magnesium sulfate and concentrated. The residue is chromatographed on silica gel using toluene/ethyl acetate/methanol/conc. ammonia=6/3.5/0.5/0.05. The crude product is digested with diethyl ether. 14.16 g (76%) of the title compound are obtained as a crystalline solid, which is used without further purification.

F. [4-(4-Chlorobutoxy)-3-methylpyridin-2-ylmethyl]-(5-chloro-2,6-dimethylpyrimidin-4-yl)amine The product is prepared from 15 g (52.7 mmol) of 4-(4-chlorobutoxy)-2-chloromethyl-3-methylpyridine hydrochloride, 12.71 g (79 mmol) of 4-amino-5-chloro-2,6-dimethylpyrimidine and 2.32 g (57.97 mmol) of sodium hydride (60% strength in paraffin) analogously to starting materials A, D and E. 13.35 g (69%) of the title compound are obtained as a crystalline solid, which is used without further purification.

G. {3-Chloro-4-[(2-chloroethyl)methylamino]pyridin-2-ylmethyl}-(5-chloro-2,6-dimethyl-pyrimidin-4-yl)amine 0.75 g (4.76 mmol) of 4-amino-5-chloro-2,6-dimethylpyrimidine is dissolved in 20 ml of dimethylformamide under a nitrogen atmosphere. 0.42 g of sodium hydride (60% strength in paraffin) is added in portions with vigorous stirring. The suspension is stirred at room temperature for 30 minutes. A solution of 1.0 g (4.59 mmol) of (3-chloro-2-chloromethylpyridin-4-yl)-(2-chloroethyl)methylamine in dimethylformamide (10 ml) is then added dropwise in the course of 30 minutes and the mixture is stirred at room temperature for a further 30 minutes. The mixture is cooled to 0° C. and cautiously treated with water (100 ml) with vigorous stirring. It is then extracted with 3×50 ml of ethyl acetate. The organic extracts are washed with 50 ml of water, dried over magnesium sulfate and concentrated. The residue is purified by chromatography on silica gel (eluent: toluene/dioxane=2/1). The fractions of $R_f$=0.5 are concentrated. 0.6 g (41%) of the title compound is isolated as a colorless solid, which is used without further purification.

H. 2-[(3-Chloro-2-chloromethylpyridin-4-yl)methylamino]ethanol

A solution of 2.6 ml (35.4 mmol) of thionyl chloride in 10 ml of dichloromethane is added dropwise with ice-cooling in the course of 20 minutes to a solution of 3.5 g (16.1 mmol) of 2-[(3-chloro-2-hydroxymethylpyridin-4-yl)methylamino]ethanol in 50 ml of anhydrous dichloromethane. The mixture is then warmed to room temperature and stirred for 30 minutes. The solution is then treated with 100 ml of water with vigorous stirring and neutralized using solid sodium hydrogencarbonate. The aqueous phase is extracted with 3×20 ml of dichloromethane. The organic extracts are dried over magnesium sulfate and concentrated 3.32 g (88%) of the title compound are obtained. This product is employed directly for further reaction without additional purification.

I. 2-(3-{2-[(5-Chloro-2,6-dimethylpyrimidin-4-ylamino)methyl]-3-methylpyridin-4-ylsulfanyl}propyl)isothiuronium chloride

I1. [4-(3-Chloropropylsulfanyl)-3-methylpyridin-2-ylmethyl]-(5-chloro-2,6-dimethylpyrimidin-4-yl)amine 4.6 g of sodium hydride (60% strength in paraffin) are suspended in 20 ml of dimethylformamide under a nitrogen atmosphere and a solution of 20.1 g (125.1 mmol) of 4-amino-5-chloro-2,6-dimethylpyrimidine in 100 ml of dimethylformamide are added dropwise in the course of 40 minutes. The suspension is stirred at room temperature for one hour. 30 g (104.3 mmol) of 2-chloromethyl-4-(3-chloropropylthio)-3-methylpyridine hydrochloride are then dissolved in 100 ml of sodium hydrogen-carbonate solution and 50 ml of dichloromethane with vigorous stirring. The aqueous phase is separated off and extracted with 2×50 ml of dichloromethane. The organic extracts are washed with 50 ml of water, dried over magnesium sulfate and concentrated. The violet oil obtained is dissolved in 15 ml of dimethylformamide and added dropwise to the previously prepared solution in the course of 45 minutes. The mixture is stirred overnight at room temperature. It is cautiously treated with water (150 ml) with vigorous stirring. It is then extracted with 3×50 ml of dichloromethane. The organic extracts are washed with 50 ml of water, dried over magnesium sulfate and concentrated. The residue is purified by chromatography on silica gel (eluent: toluene/ethyl acetate/methanol/conc. ammonia=6/3.6/0.4/0.05. After concentrating the combined fractions, a crystallizate is obtained which is digested with diethyl ether. After filtration and drying of the precipitate, 16.5 g (43%) of the title compound are isolated as a colorless solid which is used without further purification. I2. 2-(3-{2-[(5-Chloro-2,6-dimethylpyrimidin-4-ylamino)methyl]-3-methylpyridin-4-ylsulfanyl}-propyl)isothiuronium chloride 16.5 g (44.4 mmol) of [4(3-chloropropylsulfanyl)-3-methylpyridin-2-ylmethyl]-(5-chloro-2,6-dimethylpyrimidin-4-yl)amine and 10.2 g (133.3 mmol) of thiourea are suspended in 160 ml of n-propanol and refluxed for 26 hours. The suspension is then filtered and the precipitate is washed with n-propanol. After drying the precipitate, 17.4 g (88%) of the title compound are obtained. This product is employed directly for further reaction without additional purification.

J. 2-Chloromethyl-3-methyl-4-{2-[2-(2,2,2-trifluoroethoxy)ethoxy]ethylsulfanyl}pyridine

J1. 2-(2-(2,2,2-Trifluoroethoxy)ethoxy)ethyltoluene4-sulfonyl chloride 3.2 g (16.8 mmol) of toluene-4-sulfonyl chloride are added in portions to a solution of 3.0 g (15.9 mmol) of 2-(2-(2,2,2-trifluoroethoxy)ethoxy)ethanol in 15 ml of pyridine. The mixture is stirred at 40° C. for one hour. It is then concentrated and the residue is taken up in ethyl acetate (50 ml) and water (50 ml). The aqueous phase is extracted with 3×50 ml of ethyl acetate. The organic extracts are dried over magnesium sulfate and concentrated. 4.0 g (76%) of the title compound are obtained as a pale yellow oil, which is used without further purification.

J2. (3-Methyl-4-{2-[2-(2,2,2-trifluoroethoxy)ethoxy)ethylsulfanyl}pyridin-2-yl)methanol 5 ml (12 mmol) of a 6 N sodium hydroxide solution are added dropwise under a nitrogen atmosphere in the course of 30 minutes to a suspension of 1.3 g (3.8 mmol) of 2-(2-(2,2,2-trifluoroethoxy)ethoxy)ethyltoluene-4-sulfonyl chloride and 1.1 g (4.70 mmol) of 2-(2-hydroxymethyl-3-methylpyridin-4-yl)isothiuronium chloride in ethanol (10 ml). The suspension is stirred at room temperature for one hour. It is then concentrated and the residue is taken up in 30 ml of water and 30 ml of ethyl acetate. The aqueous phase is extracted with 3×30 ml of ethyl acetate. The organic extracts are washed with 20 ml of water, dried over magnesium sulfate and concentrated. The residue is purified by chromatography on silica gel (eluent: toluene/ethyl acetate= 1/1). The fractions of $R_f$=0.46 are concentrated. 0.85 g (64%) of the title compound is isolated as a colorless solid, which is used without further purification.

J3. 2-Chloromethyl-3-methyl-4-{2-[2-(2,2,2-trifluoroethoxy)ethoxy)ethylsulfanyl}pyridine A solution of 0.4 g (3.42 mmol) of thionyl chloride in 5 ml of dichloromethane is added dropwise with ice-cooling in the course of 20 minutes to a solution of 0.8 g (2.46 mmol) of (3-methyl-4-{2-[2-(2,2,2-trifluoroethoxy)ethoxy]ethylsulfanyl}pyridin-2-yl)methanol in 10 ml of anhydrous dichloromethane. The mixture is then warmed to room temperature and stirred for 30 minutes. The solution is then treated with water with vigorous stirring and neutralized with solid sodium hydrogencarbonate. The aqueous phase is extracted with 3×20 ml of dichloromethane. The organic extracts are dried over magnesium sulfate and concentrated. 0.84 g (99%) of the title compound is obtained. This product is employed directly for further reaction without additional purification

K. [4-(4-Chlorobutoxy)-3-methylpyridin-2-ylmethyl]-(5-chloro-2,6-dimethylpyrimidin-4-yl)amine

K1. 4-(4-Hydroxybutoxy)-2,3-dimethylpyridine N-oxide 24.4 g (609.1 mmol) of sodium hydride (60% strength in paraffin) are added in portions to 320.2 g (3.55 mol) of butanediol under a nitrogen atmosphere. The mixture is stirred at room temperature over the weekend. The mixture is then heated to 100° C. and 80 g (507.6 mmol) of 4-chloro-2,3-dimethylpyridine N-oxide are added. The mixture is first stirred at 100° C. for 2 hours and then at 120° C. for a further 2 hours. It is then concentrated in a high vacuum. The residue is suspended in 600 ml of ethanol and heated. After filtering off the inorganic salts with suction, the filtrate is concentrated. The residue is purified by chromatography on silica gel (eluent: ethyl acetate→ethyl acetate/methanol=9:1). The eluate is concentrated. The residue is then digested with diethyl ether. After filtration and drying of the precipitate, 67.4 g (63%) of the title compound are obtained as a colorless solid, which is used without further purification.

K2. 4-(2-Hydroxymethyl-3-methylpyridin-4-yloxy)butan-1-ol 30 g (0.14 mol) of 4-(4-hydroxybutoxy)-2,3-dimethylpyridine N-oxide are added in portions at 50° C. to 174 g (1.7 mol) of acetic anhydride in the course of one hour. After addition is complete, the mixture is heated to 90° C. and stirred for a further 8 hours. The mixture is then concentrated. The residue obtained is dissolved in 150 ml of methanol and 38.3 g (0.71 mol) of sodium methoxide solution (30% strength in methanol) are added. The mixture is stirred at room temperature for one hour. It is then concentrated. The residue is taken up in half-saturated sodium chloride solution and dichloromethane with vigorous stirring. The aqueous phase is extracted with 3×50 ml of dichloromethane. The organic extracts are dried over magnesium sulfate and concentrated. The residue is digested with diethyl ether. After filtration and drying of the precipitate, 21.6 g (72%) of the title compound are obtained. This product is employed directly for further reaction without additional purification.

K3. 4-(4-Chlorobutoxy)-2-chloromethyl-3-methylpyridine hydrochloride

A solution of 33.8 g (284 mmol) of thionyl chloride in 25 ml of dichloromethane is added dropwise with ice-cooling in the course of 30 minutes to a solution of 15 g (71 mmol) of 4-(2-hydroxymethyl-3-methylpyridin-4-yloxy)butan-1-ol in 200 ml of anhydrous dichloromethane. The mixture is then warmed to room temperature and stirred for 20 hours. The mixture is then concentrated and coevaporated with 3×20 ml of toluene. The precipitate obtained is digested with diethyl ether. After filtration and drying, 20.8 g (100%) of the title compound are obtained as a colorless solid. This product is employed directly for further reaction without additional purification.

K4[4-(4-Chlorobutoxy)-3-methylpyridin-2-ylmethyl]-(5-chloro-2,6-dimethylpyrimidin-4-yl)amine 2.3 g of sodium hydride (60% strength in paraffin) are suspended in 10 ml of dimethylformamide under a nitrogen atmosphere and a solution of 12.7 g (79 mmol) of 4-amino-5-chloro-2,6-dimethylpyrimidine in 70 ml of dimethylformamide is added dropwise in the course of 40 minutes. The suspension is then stirred at room temperature for 2 hours. 15 g (52.7 mmol) of 4-(4-chlorobutoxy)-2-chloromethyl-3-methylpyridine hydrochloride are then suspended in 100 ml of dichloromethane and the free base is liberated using saturated aqueous sodium hydrogencarbonate solution. The organic phase is dried over magnesium sulfate and concentrated. The residue is taken up in 100 ml of dimethylformamide and added dropwise to the previously prepared suspension. After 45 minutes, the mixture is concentrated in a high vacuum. The residue obtained is cautiously treated with water (100 ml) with vigorous stirring. It is then extracted with 3×50 ml of dichloromethane. The organic extracts are washed with 50 ml of water, dried over magnesium sulfate and concentrated. The residue is purified by chromatography on silica gel (eluent: toluene/ethyl acetate/methanol/conc. ammonia=6/3.5/0.5/0.05). The eluate is concentrated. 13.5 g (69%) of the title compound are isolated as a colorless solid, which is used without further purification.

L. [4-(3-Chloropropylsulfanyl)-3-methylpyridin-2-ylmethyl]-(5-chloropyrimidin-4-yl)amine A solution of 2.7 g (20.85 mmol) of 4-amino-5-chloropyrimidine in 20 ml of dimethylformamide is added dropwise to a suspension of 0.75 g (18.25 mmol) of sodium hydride (60% strength in paraffin) in 5 ml of dimethylformamide. The mixture is stirred at room temperature for 20 minutes. A solution of 5 g (17.38 mmol) of 2-chloromethyl-4-(3-chloropropylsulfanyl)-3-methylpyridine in 5 ml of dimethylformamide is then added dropwise in the course of 30 minutes and the mixture is then stirred at room temperature for 4 hours. It is concentrated in a high vacuum and the residue is taken up in 150 ml of water and 100 ml of dichloromethane with vigorous stirring. The aqueous phase is extracted with 3×50 ml of dichloromethane. The organic extracts are dried over magnesium sulfate and concentrated. The residue is purified by chromatography on silica gel (eluent: toluene/ethyl acetate/methanol/conc. ammonia=6/3.5/0.5/0.05). The eluate is concentrated and the residue is then digested with diethyl ether. After filtration and drying of the precipitate, 2.8 g (47%) of the title compound are obtained as a colorless solid, which is used without further purification.

M. 5-[3-(2-Chloromethyl-3-methylpyridin-4-ylsulfanyl)propylsulfanylmethyl]-3-methyloxazolidin-2-one

M1. 5-Chloromethyl-3-methyloxazolidin-2-one 3.2 g (81.2 mmol) of sodium hydride (60% strength in paraffin) are suspended in 150 ml of N-methylpyrrolidone under a nitrogen atmosphere. A solution of 10 g (73.7 mmol) of 5-chloromethyloxazolidin-2-one in 40 ml of N-methylpyrrolidone is then added dropwise in the course of 30 minutes. The suspension is stirred at room temperature for one hour. 11.6 g (81.2 mmol) of methyl iodide in 10 ml of N-methylpyrrolidone are then added dropwise. The mixture is then stirred at room temperature for 4 hours. The mixture is concentrated in a high vacuum. The residue obtained is cautiously treated with water (100 ml) with vigorous stirring. It is then extracted with 3×50 ml of dichloromethane. The organic extracts are washed with 50 ml of water, dried over magnesium sulfate and concentrated. 7.5 g (68%) of the title compound are obtained as an oil, which is used without further purification.

M2. 5[3(2-Hydroxymethyl-3-methylpyridin-4-ylsulfanyl)propylsulfanylmethyl]-3-methyloxazolidin-2-one 7.5 g (28.2 mmol) of 14-(3-mercaptopropylsulfanyl)-3-methylpyridin-2-yl)methanol hydrochloride and 11.7 g (84.72 mmol) of potassium carbonate are suspended in 100 ml of dimethylformamide under a nitrogen atmosphere. After 30 minutes, 7.7 g (31.1 mmol) of 5-chloromethyl-3-methyloxazolidin-2-one are added. The mixture is then stirred at 60° C. for 3 hours. It is allowed to cool to room temperature and is filtered. The filtrate is concentrated in a high vacuum. The residue is taken up in 100 ml of water. It is then extracted with 3×30 ml of dichloromethane. The organic extracts are washed with 50 ml of water, dried over magnesium sulfate and concentrated. The residue is purified by chromatography on silica gel (eluent: toluene/dioxane/methanol/conc. ammonia=5/4/1/0.05). The fractions of $R_f$=0.5 are concentrated. 8.1 g (84%) of the title compound are obtained as a colorless oil, which is used without further purification.

M3. 5-[3-(2-Chloromethyl-3-methylpyridin-4-ylsulfanyl)propylsulfanylmethyl]-3-methyloxazolidin-2-one A solution of 3.1 g (25.6 mmol) of thionyl chloride in 20 ml of dichloromethane is added dropwise with ice-cooling in the course of 20 minutes to a solution of 8 g (23.3 mmol) of 5-[3-(2-hydroxymethyl-3-methylpyridin-4-ylsulfanyl)propylsulfanylmethyl]-3-methyloxazolidin-2-one in 80 ml of anhydrous dichloromethane. The mixture is then warmed to room temperature and stirred for one hour. The solution is then treated with 100 ml of water with vigorous stirring and neutralized using solid sodium hydrogencarbonate. The aqueous phase is extracted with 3×50 ml of dichloromethane. The organic extracts are dried over magnesium sulfate and concentrated. 5.0 g (59%) of the title compound are obtained as a yellow oil. This product is employed directly for further reaction without additional purification.

N. {3-Chloro-4-[(3-chloropropyl)methylamino]pyridin-2-ylmethyl)-(5-chloro-2,6-dimethylpyrimidin-4-yl)amine

N1. (3-Chloro-2-chloromethylpyridin-4-yl)-(3-chloropropyl)methylamine hydrochloride A solution of 23 ml (317 mmol) of thionyl chloride in 80 ml of dichloromethane is added dropwise with ice-cooling in the course of 20 minutes to a solution of 35.3 g (153 mmol) of (3-chloro-2-hydroxymethylpyridin-4-yl)methylaminopropanol in 300 ml of anhydrous dichloromethane. The mixture is then warmed to room temperature and stirred for one hour. It is then concentrated and the residue is taken up in 200 ml of 2 N NaOH solution. The aqueous phase is extracted with 3×150 ml of dichloromethane. The organic extracts are dried over magnesium sulfate and concentrated. The oil obtained is dissolved in methanol. It is then precipitated with ethereal HCl. After filtration and drying of the precipitate, 27.4 g (67%) of the title compound are obtained. This product is employed directly for further reaction without additional purification.

N2. {3-Chloro-4-[(3-chloropropyl)methylamino]pyridin-2-ylmethyl}-(5-chloro-2,6-dimethylpyrimidin-4-yl)amine 1.0 g (6.3 mmol) of 4-amino-5-chloro-2,6-dimethylpyrimidine is dissolved in 20 ml of dimethylformamide under a nitrogen atmosphere. 0.21 g of sodium hydride (80% strength in paraffin) is added in portions with vigorous stirring. The suspension is then stirred at room temperature for 30 minutes. A solution of 2.1 g (6.1 mmol) of (3-chloro-2-chloromethylpyridin-4-yl)-(3-chloropropyl)methylamine in dimethylformamide (10 ml) is then added dropwise in the course of 30 minutes and stirred at room temperature for one hour. The mixture is cooled to 0° C. and cautiously treated with water (100 ml) with vigorous stirring. It is then extracted with 3×50 ml of ethyl acetate. The organic extracts are washed with 50 ml of water, dried over magnesium sulfate and concentrated. The residue is purified by chromatography on silica gel (eluent: toluene/dioxane=4/1). The fractions of $R_f$=0.53 are concentrated. 1.2 g (49%)

of the title compound are isolated as a colorless solid, which is used without further purification.

O. 5-[3-(2-Chloromethyl-3-methylpyridin-4-ylsulfanyl)propylsulfanylmethyl]-3-(4-methoxyphenyl)oxazolidin-2-one

O1. 5-[3-(2-Hydroxymethyl-3-methylpyridin-4-ylsulfanyl)propylsulfanylmethyl]-3(4-methoxyphenyl)oxazolidin-2-one 1.27 g (5.0 mmol) of [4-(3-mercaptopropylsulfanyl)-3-methylpyridin-2-yl]methanol are dissolved in 10 ml of dimethylformamide under a nitrogen atmosphere and 0.16 g of sodium hydride (80% strength in paraffin) is added in portions with vigorous stirring. The suspension is then stirred at room temperature for one hour. A solution of 1.0 g (4.1 mmol) of 5-chloromethyl-3-(4-methoxyphenyl) oxazolidin-2-one in dimethylformamide (10 ml) is added in the course of 30 minutes and the mixture is stirred at room temperature for one hour. The mixture is cooled to 0° C. and cautiously treated with water (100 ml) with vigorous stirring. It is then extracted with 3×50 ml of ethyl acetate. The organic extracts are washed with 50 ml of water, dried over magnesium sulfate and concentrated. The residue is purified by chromatography on silica gel (eluent: ethyl acetate). The fractions of $R_f$=0.23 are concentrated. After crystallization from isopropanol, 0.81 g (49%) of the title compound is obtained as a colorless solid which is used without further purification.

O2. 5-[3-(2-Chloromethyl-3-methylpyridin-4-ylsulfanyl)propylsulfanylmethyl]-3-(4-methoxyphenyl)oxazolidin-2-one A solution of 0.25 g (2.0 mmol) of thionyl chloride in 5 ml of dichloromethane is added dropwise at room temperature in the course of 20 minutes to a solution of 0.74 g (1.7 mmol) of 5-[3-(2-hydroxymethyl-3-methylpyridin-4-ylsulfanyl)propylsulfanylmethyl]-3-(4-methoxyphenyl) oxazolidin-2-one in 5 ml of anhydrous dichloromethane and stirred overnight. The solution is then neutralized with sodium hydrogencarbonate solution with vigorous stirring. The mixture is concentrated to half the volume, a precipitate being deposited. After filtration and drying of the precipitate, 0.75 g (97%) of the title compound is obtained. This product is employed directly for further reaction without additional purification.

P. (5-Chloro-2,6-dimethyl-pyrimidin-4-yl)-{4-[2-(2-chloro-ethoxy)-ethoxy]-3-methyl-pyridin-2-ylmethyl}-amine The compound is obtained analogously to Example K, starting with diethylenglycol and 4-chloro-2,3-dimethyl-pyridine-N-oxide

Q. (5-Chloro-2,6-dimethyl-pyrimidin-4-yl)-[4-(2-chloro-ethoxy)-3-methyl-pyridin-2-ylmethyl]-amine The compound is obtained analogously to Example K, starting with ethylenglycol and 4-chloro-2,2-dimethyl-pyridine-N-oxide

R. (5-Chloro-2,6-dimethyl-pyrimidin-4-yl)-[4-(3chloropropoxy)-3-methyl-pyridin-2-ylmethyl]-amine The compound is obtained analogously to Example K, starting with 1,3-propandiol and 4-chloro-2,3-dimethyl-pyridine-N-oxide

S. 5-Piperazin-1-ylmethyl-3-pyridin-4-ylmethyl-oxazolidin-2-one

S1. 5-Chloromethyl-3-pyridin-4-ylmethyl-oxazolidin-2-one

Sodium hydride (5.8 g, 0.242 mol) is suspended in 200 ml of NMP (N-methylpyrrolidone) under an atmosphere of nitrogen. A solution of (±)-5-chloromethyl-2-oxazolidinone (15 g, 0.110 mol) in 60 ml of NMP is added slowly during 45 minutes. The mixture is stirred for one hour at room temperature. 4-Picolylchloride-hydrochloride (20.46 g, 0.121 mol) is added in small portions during one hour. The mixture is stirred for 18 hours at room temperature. NMP is evaporated in vacuo The residue is diluted with 250 ml of water and extracted four times with 50 ml of dichloromethane. The combined organic phases are washed with water and concentrated in vacuo. The residue is purified by chromatography over silica with ethylacetate/methanol= 15/1 to yield the title compound as yellow oil (24 g, 96%).

S2. 5-Piperazin-1-ylmethyl-3-pyridin-4-ylmethyl-oxazolidin-2-one

5-Chloromethyl-3-pyridin-4-ylmethyl-oxazolidin-2-one (18 g, 79.41 mmol), piperazine (35 g, 397 mmol) and $K_2CO_3$ (55 g, 397 mmol) are refluxed in 350 ml of acetonitril together with a catalytic amount of sodium iodide for 24 hours. The mixture is filtered and the acetonitril is evaporated in vacuo. The residue is purified by chromatography over silica with ethylacetate/methanol=15/1 to yield the title compound as yellow oil (24 g, 96%).

T. (2-Chloromethyl-3-methyl-4-[3-(3-nitro-thiophen-2-ylsulfanyl)-propylsulfanyl]-pyridine-hydrochloride

T1. (2-hydroxymethyl-3-methyl-4-[3-(3-nitro-thiophen-2-ylsulfanyl)-propylsulfanyl]-pyridine

[4-(3-Mercapto-propylsulfanyl)-3-methyl-pyridin-2-yl]-methanol-hydrochloride (10 g, 37.69 mmol), 2-chloro-3-nitrothiophene (6.47 g, 39.57 mmol) and $K_2CO_3$ (15.63 g, 113.07 mmol) are stirred in 100 ml of DMF for three hours at room temperature. The mixture is filtered and the DMF is evaporated in vacuo. The residue is diluted with 150 ml of water and extracted five times with 30 ml of a mixture of chloroform/methanol=10/1. The combined organic phases are washed with water and concentrated in vacuo. The crude product is triturated with diethyl ether to give the title compound (5.1 g, 38%). Mp.: 134–138° C.

T2. (2-Chloromethyl-3-methyl-4-[3-(3-nitro-thiophen-2-ylsulfanyl)-propylsulfanyl]-pyridine-hydrochloride (2-Hydroxymethyl-3-methyl-4-[3-(3-nitro-thiophen-2-ylsulfanyl)-propylsulfanyl]-pyridine (4 g, 10.94 mmol) is suspended in 60 ml of dichloromethane. Thionylchloride (1.69 g, 14.23 mmol) in 10 ml of dichloromethane is added slowly during 20 minutes. The mixture is stirred for two hours at room temperature. The mixture is concentrated in vacuo to give the title compound, which is used without further purification.

U. (5-Chloro-2,6-dimethyl-pyrimidin-4-yl)-{4-[3-(2-chloro-ethylsulfanyl)-propylsulfanyl]-3-methyl-pyridin-2-ylmethyl}-amine-hydrochloride 2-(3-{2-[(5-Chloro-2,6-dimethyl-pyrimidin-4-ylamino)-methyl]-3-methyl-pyridin-4-ylsulfanyl}-propylsulfanyl)- ethanol (12.3 g, 29.78 mmol) is suspended in 125 ml of dichloromethane. Thionylchloride (4.6 g, 38.71 mmol) is slowly added. The mixture is stirred for three hours at room temperature. The mixture is concentrated in vacuo and coevaporated two times with 20 ml of toluene. The crude product is triturated with diethylether to give the title compound (14.74 g, 100%).

V. (5-Chloro-2,6-dimethyl-pyrimidin-4-yl)-{4-[2-(2-chloro-ethoxy)-ethylsulfanyl]-3-methyl-pyridin-2-ylmethyl}-amine

V1. {4-[2-(2-Chloro-ethoxy)-ethylsulfanyl]-3-methyl-pyridin-2-yl}-methanol

The compound is obtained analogously to Example 28 from 2-(2-hydroxymethyl-3-methyl-pyridin-4-yl)-isothiourea-hydrochloride (75 g, 0.277 mol) and 2,2'-dichlorodiethylether (158.8 g, 1.11 mol) to give the title compound (40.36 g, 56%).

V2. 4-[2-(2-Chloro-ethoxy)ethylsulfanyl]-2-chloromethyl-3-methyl-pyridine-hydrochloride {4-[2-(2-Chloro-ethoxy)-ethylsulfanyl]-3-methyl-pyridin-2-yl}-methanol (35 g, 0.133 mol) is added slowly during one hour to 103 g of thionyl chloride. The mixture is stirred for two hours at room temperature and afterwards concentrated in vacuo. The residue is co-evaporated three times with 30 ml of Toluene and dried in vacuo. The crude product is triturated with diethyl ether to give the title compound (40.17 g, 95%).

V3. (5-Chloro-2,6-dimethyl-pyrimidin-4-yl)-{4-[2-(2-chloro-ethoxy)-ethylsulfanyl]-3-methyl-pyridin-2-ylmethyl}-amine The compound is obtained analogously to Example E from 4-[2-(2-chloro-ethoxy)-ethylsulfanyl]-2-chloromethyl-3-methyl-pyridine-hydrochloride (25 g, 78.94 mmol) and 4-amino-5-chloro-2,6-dimethyl-pyrimidine (19 g, 118.41 mmol) to give the title compound (23.1 g, 73%).

W. (5-Chloro-2,6-dimethyl-pyrimidin-4-yl)-(4-{2-[2-(2-chloro-ethoxy)-ethoxy]-ethylsulfanyl}-3-methyl-pyridin-2-ylmethyl)-amine

W1. 2-{2-[2-(2-Hydroxymethyl-3-methyl-pyridin-4-ylsulfanyl)-ethoxy]-ethoxy}-ethanol The compound is obtained analogously to Example 28 from 2-(2-hydroxymethyl-3-methyl-pyridin-4-yl)-isothiourea-hydrochloride (15 g, 55.5 mmol) and 2-[2-(2-chloroethoxy)-ethoxy]-ethanol (19.1 g, 111 mmol) to give the title compound (15.9 g, 100%).

W2. 4-{2-[2-(2-Chloro-ethoxy)-ethoxy]-ethylsulfanyl}-2-chloromethyl-3-methyl-pyridine-hydrochloride The compound is obtained analogously to Example V2 from 2-{2-[2-(2-hydroxymethyl-3-methyl-pyridin-4-ylsulfanyl)-ethoxy]-ethoxy}-ethanol (15.9 g, 55.5 mmol) and thionyl chloride (30 g, 0.252 mol) to give the title compound (20.0 g, 100%).

W3. (5-Chloro-2,6-dimethyl-pyrimidin-4-yl)-(4-{2-[2-(2-chloro-ethoxy)-ethoxy]-ethylsulfanyl}-3-methyl-pyridin-2-ylmethyl)-amine The compound is obtained analogously to Example E from 4-{2-[2-(2-chloro-ethoxy)-ethoxy]-ethylsulfanyl}-2-chloromethyl-3-methyl-pyridine-hydrochloride (15 g, 41.58 mmol) and 4-amino-5-chloro-2,6-dimethyl-pyrimidine (10 g, 62.37 mmol) to give the title compound (7.52 g, 41%).

X. 2-Chloromethyl-3-methyl-4-(1-methyl-piperidin-3-ylmethylsulfanyl)-pyridine-hydrochloride

X1. [3-Methyl-4-(1-methyl-piperidin-3-ylmethylsulfanyl)-pyridin-2-yl]-methanol The compound is obtained analogously to Example 28 from 2-(2-hydroxymethyl-3-methyl-pyridin-4-yl)-isothiourea-hydrochloride (15 g, 55.5 mmol) and 3-chloromethyl-N-methylpiperidine (11.5 g, 61.07 mmol) to give the title compound (2.86 g, 20%).

X2. 2-Chloromethyl-3-methyl-4-(1-methyl-piperidin-3-ylmethylsulfanyl)-pyridine-hydrochloride The compound is obtained analogously to Example V2 from [3-methyl-4-(1-methyl-piperidin-3-ylmethylsulfanyl)-pyridin-2-yl]-methanol (2.8 g, 10.92 mmol) and thionyl chloride (2 g, 16.38 mol) to give the title compound (3.39 g, 100%).

Y. (5-Chloro-pyrimidin-4-yl)-[3-methyl-4-(3-piperazin-1-yl-propylsulfanyl)-pyridin-2-ylmethyl]-amine The compound is obtained analogously to Example B from [4-(3-chloro-propylsulfanyl)-3-methyl-pyridin-2-ylmethyl]-(5-chloro-pyrimidin-4-yl)-amine (2.5 g, 7.28 mmol) and piperazine (3.8 g, 43.69 mmol) to give the title compound (2.8 g, 98%).

Z. (5-Chloro-2,6-dimethyl-pyrimidin-4-yl)-(4-chloro-3-methyl-pyridin-2-ylmethyl)-amine The compound is obtained analogously to Example E from 4-chloro-2-chloromethyl-3-methyl-pyridine-hydrochloride (30 g, 141.16 mmol) and 4-amino-5-chloro-2,6-dimethyl-pyrimidine (34 g, 211.7 mmol) to give the title compound (26.9 g, 64%).

AA. [4-(2-Chloro-ethoxy)-3-methyl-pyridin-2-ylmethyl]-(5-chloro-pyrimidin-4-yl)-amine The compound is obtained analogously to Example K starting with ethylenglycol and 4-chloro-2,3-dimethyl-pyridine-N-oxide and reaction of 4-amino-5-chloro-pyrimidine with 4-(2-chloro-ethoxy)-2-chloromethyl-3-methyl-pyridine in the last step.

AB. (5-Chloro-pyrimidin-4-yl)-[4-(3-chloro-propoxy)-3-methyl-pyridin-2-ylmethyl]-amine The compound is obtained analogously to Example K starting with 1,3-propanediol and 4-chloro-2,3-dimethyl-pyridine-N-oxide and reaction of 4-amino-5-chloro-pyrimidine with 4-(3-chloro-propoxy)-2-chloromethyl-S-methyl-pyridine in the last step.

AC. Methanesulfonic acid 2-{2-[(5-chloro-pyrimidin-4-ylamino)-methyl]-3-methyl-pyridin-4-ylsulfanyl}-ethyl ester 2-{2-[(5-Chloro-pyrimidin-4-ylamino)-methyl]-3-methyl-pyridin-4-yloxy}-ethanol (3 g, 10.11 mmol) is dissolved in a mixture of dichloromethane (30 ml) and pyridine (1.2 g, 15.17 mmol). Methanesulfonic acid anhydride (2.64 g, 15.17 mmol) is added. The mixture is stirred for one hour and afterwards poured on 100 ml of water. The pH is adjusted to a value of 8 by addition of a solution of NaHCO$_3$. The mixture is extracted three times with 30 ml of dichloromethane. The combined organic phases are washed with water (5×20 ml) and concentrated in vacuo. The crude product is triturated with diethyl ether to give the title compound (3.31 g, 88%).

AD. 2-Chloromethyl-4-(furan-2-ylmethylsulfanyl)-3-methyl-pyridine-hydrochloride

AD1. 4-(Furan-2-ylmethylsulfanyl)-2,3-dimethyl-pyridin-N-oxide

4-Chloro-2,3-dimethyl-pyridine-N-oxide (1200 g, 7.61 mol), furfurylmercaptane (790 ml, 7.58 mol) and sodium hydroxide (365 g, 9.12 mol) are dissolved in 8 l of water under an atmosphere of nitrogen. The mixture is stirred at 65° C. for 8 hours. After cooling to room temperature the crude product is filtered off and dried in vacuo to give the title compound (1493 g, 83%).

AD2. 2-Chloromethyl-4-(furan-2-ylmethylsulfanyl)-3-methyl-pyridine-hydrochloride The compound is obtained analogously to Examples K2 and K3, starting with 4-(furan-2-ylmethylsulfanyl)-2,3-dimethyl-pyridin-N-oxide.

COMMERCIAL UTILITY

The excellent activity of compounds of the formula I and their salts against Helicobacter bacteria allows their use in human medicine as active compounds for the treatment of illnesses which are based on Helicobacter bacteria.

The invention therefore further relates to a process for the treatment of mammals, in particular humans, who are suffering from illnesses which are based on Helicobacter bacteria. The process comprises administering to the sick individual a therapeutically efficacious and pharmacologically tolerable amount of one or more compounds of the formula I and/or their pharmacologically tolerable salts.

The invention moreover relates to the compounds of the formula I and their pharmacologically tolerable salts for use in the treatment of illnesses which are based on Helicobacter bacteria.

The invention also comprises the use of compounds of the formula I and their pharmacologically tolerable salts in the production of medicaments which are employed for the control of those illness which are based on Helicobacter bacteria.

The invention further relates to medicaments for the control of Helicobacter bacteria, which contain one or more compounds of the general formula I and/or their pharmacologically tolerable salts.

Of the Helicobacter strains against which the compounds of the formula I prove active, the strain Helicobacter pylori may be mentioned in particular.

The medicaments are prepared by processes known per se, which are familiar to the person skilled in the art. As medicaments, the pharmacologically active compounds of the formula I and their salts(=active compounds) are either used as such, or preferably employed in combination with suitable pharmaceutical auxiliaries, e.g. in the form of tablets, coated tablets, capsules, emulsions, suspensions, gels or solutions, the active compound content advantageously being between 0.1 and 95%.

Auxiliaries which are suitable for the desired pharmaceutical formulations are familiar to the person skilled in the art on account of his/her expert knowledge. In addition to solvents, gel-forming agents, tablet auxiliaries and other active compound carriers, it is possible to use, for example, antioxidants, dispersants, emulsifiers, antifoams, flavor corrigents, preservatives, solubilizers, colorants or permeation promoters and complexing agents (e.g. cyclodextrins).

The active compounds can be administered, for example, parenterally (e.g. intravenously) or in particular orally.

In general, the active compounds are administered in human medicine in a daily dose of approximately 0.2 to 50, preferably 1 to 30, mg/kg of body weight, if appropriate in the form of a number of, preferably 2 to 6, individual doses to achieve the desired result.

The compounds according to the invention can also be administered in a fixed or free combination together with a substance neutralizing gastric acid and/or inhibiting gastric acid secretion and/or with a substance suitable for the conventional control of Helicobacter pylori.

Substances neutralizing gastric acid which may be mentioned are, for example, sodium hydrogencarbonate or other antacids (such as aluminum hydroxide, magnesium aluminate or magaldrate). Substances inhibiting gastric acid secretion which may be mentioned are, for example, H$_2$ blockers (e.g. cimetidine, ranitidine), H$^+$/K$^+$ ATPase inhibitors (e.g. lansoprazole, omeprazole, rabeprazole or, in particular, pantoprazole) and so-called peripheral anticholinergics (e.g. pirenzepine, telenzepine).

Substances suitable for the conventional control of Helicobacter pylori which may be mentioned are, in particular, antimicrobially active substances such as, for example, penicillin G, gentamycin, erythromycin, clarithromycin, azithromycin, nitrofurazone, tinidazole, nirofurantoin, furazolidone, metronidazole or amoxycillin, or else alternatively bismuth salts such as, for example, bismuth citrate.

BIOLOGICAL INVESTIGATIONS

The compounds of the formula I were investigated with respect to their activity against Helicobacter pylori following the method described by Tomoyuki Iwahi et al. (Antimicrobial Agents and Chemotherapy, 1991, 490–496) using Columbia agar (Oxoid) and a growth period of 4 days. For the compounds investigated, the approximate MIC 50 values listed in Table A below resulted here (the numbers of the compounds indicated agree with the example numbers in the description).

TABLE A

| Compound No. | Appr. MIC 50 ($\mu$g/ml) |
|---|---|
| 4 | ≦0.1 |
| 5 | ≦0.1 |
| 6 | ≦0.1 |
| 7 | ≦0.1 |
| 8 | ≦0.1 |
| 9 | ≦0.1 |
| 10 | ≦0.1 |
| 12 | ≦0.1 |
| 15 | ≦0.1 |
| 16 | ≦0.1 |
| 17 | ≦0.1 |
| 18 | ≦0.1 |
| 19 | ≦0.1 |
| 20 | ≦0.1 |
| 22 | ≦0.1 |
| 23 | ≦0.1 |

TABLE A-continued

| Compound No. | Appr. MIC 50 (μg/ml) |
|---|---|
| 24 | ≦0.1 |
| 27 | ≦0.1 |
| 28 | ≦0.1 |
| 29 | ≦0.1 |
| 30 | ≦0.1 |
| 31 | ≦0.1 |
| 32 | ≦0.1 |
| 33 | ≦0.1 |
| 34 | ≦0.1 |
| 35 | ≦0.1 |
| 36 | ≦0.1 |
| 37 | ≦0.1 |
| 38 | ≦0.1 |
| 39 | ≦0.1 |
| 40 | ≦0.1 |
| 41 | ≦0.1 |
| 42 | ≦0.1 |
| 43 | ≦0.1 |
| 44 | ≦0.1 |
| 45 | ≦0.1 |
| 46 | ≦0.1 |
| 47 | ≦0.1 |
| 48 | ≦0.1 |
| 49 | ≦0.1 |
| 50 | ≦0.1 |
| 51 | ≦0.1 |
| 52 | ≦0.1 |
| 53 | ≦0.1 |
| 54 | ≦0.1 |
| 55 | ≦0.1 |
| 56 | ≦0.1 |
| 57 | ≦0.1 |
| 58 | ≦0.1 |
| 59 | ≦0.1 |
| 60 | ≦0.1 |

What is claimed is:

1. A compound of the formula I

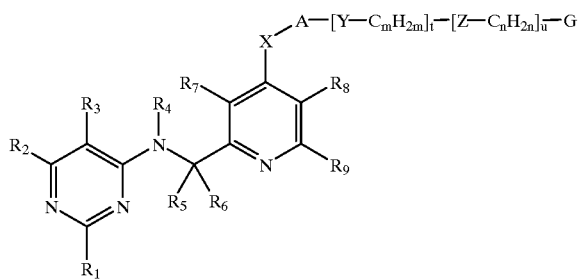

in which

R1, R2 and R3 are identical to or different from one another and are hydrogen, 1–4C-alkyl or halogen, R4 is hydrogen or 1–4C-alkyl, R5 is hydrogen or 1–4C-alkyl, R6 is hydrogen or 1–4C-alkyl, R7 is hydrogen, 1–4C-alkyl, 1–4C-alkoxy or halogen, R8 is hydrogen, 1–4C-alkyl, 1–4C-alkoxy or halogen, R9 is hydrogen or 1–4C-alkyl, A is 1–7C-alkylene, 2–7C-alkenylene, 3–7C-cycloalkylene or phenylene, G is hydrogen, hydroxyl, 1–7C-alkyl, 1–4C-alkyl which is completely or mainly substituted by fluorine, 2–7C-alkenyl, 3–7C-cycloalkyl, a mono- or di-1–4C-alkylcarbamoyl or -thiocarbamoyl group, an N-1–4C-alkyl-N'-cyanoamidino group, a 1-N-1–4C-alkylamino-2-nitroethylene group, an N-2-propynyl-N'-cyanoamidino group, an aminosulfonylamidino group, the group —N(R10)R11,

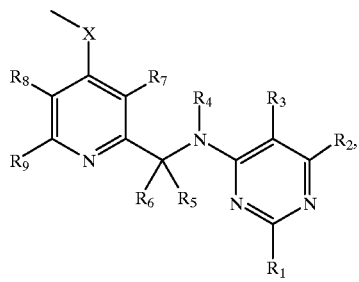

the glucopyranoside group or a cyclic system or bicyclic system which is unsubstituted or substituted by R12 and R13 and which is selected from the group consisting of benzene, naphthalene, furan, thiophene, pyrrole, oxazole, oxazoline, oxazolidinone, isoxazole, thiazole, thiazoline, isothiazole, imidazole, imidazoline, pyrazole, triazole, tetrazole, thiadiazole, thiodiazole 1-oxide, oxadiazole, pyridine, pyridine N-oxide, pyrimidine, halopyrimidine, piperidine, triazine, pyridone, benzimidazole, imidazopyridine, benzothiazole, benzoxazole, quinoline and imidazopyridazine, in which R10 is 1–7C-alkyl, 3–7C-cycloalkyl or Ar-1–4C-alkyl and R11 is 1–7C-alkyl, 3–7C-cycloalkyl or Ar-1–4C-alkyl, where Ar is phenyl, furyl, naphthyl, tetrahydronaphthyl or phenyl which is substituted by R14, R15 and R16, or in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, thiomorpholine, indoline, 1,2,3,4-tetrahydroquinoline and 1,2,3,4-tetrahydroisoquinoline, where a substituted pyrrolidino group is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl, a substituted piperidino group is substituted by one, two or three identical or different substituents selected from the group consisting of 1–4C-alkyl, 1–4C-alkoxycarbonyl, hydroxy-1–4C-alkyl, phenyl or phenyl-1–4C-alkyl, which is substituted by R14, R15 and R16, benzoyl, benzoyl substituted by halogen and carboxyl, a substituted piperazino group can be substituted in the 2-, 3-, 5- or 6-position by a 1–4C-alkyl group, and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl and carbamoyl, a substituted morpholino group is substituted by one or two identical or different 1–4C-alkyl groups, a substituted thiomorpholino group is substituted by one or two identical or different 1–4C-alkyl groups or a carboxyl group, a substituted indolin-1-yl group can be substituted in the 2- and/or 3-position by a carboxyl group or by one or two identical or different 1–4C-alkyl groups, and can be substituted in the benzo moiety by one or two identical or different substituents selected from the group consisting of 1–4C-alkyl, halogen and nitro, a substituted 1,2,3,4-tetrahydroquinoline group is substituted by one or two identical or different substituents selected from the group consisting of 1–4C-alkyl, 1–4C-alkoxycarbonyl and halogen, a substituted 1,2,3,4-tetrahydroisoquinoline group is substituted by one or two identical or different substituents selected from the group consisting of 1–4C-alkyl, carboxyl and phenyl, R12 is hydrogen, 1–4C-alkyl, hydroxyl, 1–4C-alkoxy, halogen, nitro, guanidino, carboxyl, 1–4C-alkoxycarbonyl, 1–4C-alkyl substituted by R17, phenyl substituted by R14, R15 and R16 or —N(R18)R19, R13 is hydrogen, 1–4C-alkyl, hydroxyl, 1–4C-alkoxy, halogen or trifluoromethyl, R14 is hydrogen, 1–4C-alkyl, hydroxyl, 1–4C-alkoxy, 1–4C-alkylcarbonyl, halogen, trifluoromethyl, 1–4C-alkylamino or nitro, R15 is hydrogen, 1–4C-alkyl, hydroxyl, 1–4C-alkoxy, halogen or nitro, and R16 is hydrogen or trifluoromethyl, R17 is hydroxyl, 1–4C-alkoxy, carboxyl, 1–4C-alkoxycarbonyl, pyridinyl or —N(R18)R19, where R18 is hydrogen, 1–4C-alkyl or —CO—R20 and R19 is hydrogen or 1–4C-alkyl, or where R18 and R19, together and including the nitrogen atom to which both are bonded, are a piperidino or morpholino group, R20 is hydrogen, 1–4C-alkyl or 1–4-alkoxy, X is O (oxygen), N-1–4C-alkyl, NH or S, Y is O (oxygen), N-1–4C-alkyl, NH, S, 1,4-piperazinylene or 1,4-piperidinylene, Z is O (oxygen), N-1–4C-alkyl, NH or S or CO, m is a number from 1 to 7, n is a number from 0 to 4, t is the number 0, 1 or 2 and u is the number 0 or 1, or its salts.

2. A compound of the formula I as claimed in claim 1, in which

R1, R2 and R3 are identical to or different from one another and are hydrogen, 1–4C-alkyl or halogen, R4 is hydrogen or 1–4C-alkyl, R5 is hydrogen or 1–4C-alkyl, R6 is hydrogen or 1–4C-alkyl, R7 is hydrogen, 1–4C-alkyl, 1–4C-alkoxy or halogen, R8 is hydrogen, 1–4C-alkyl, 1–4C-alkoxy or halogen, R9 is hydrogen or 1–4C-alkyl, A is 1–7C-alkylene, 2–7C-alkenylene, 3–7C-cycloalkylene or phenylene, G is hydrogen, 1–7C-alkyl, 1–4C-alkyl which is completely or mainly substituted by fluorine, 2–7C-alkenyl, 3–7C-cycloalkyl, a mono- or di-1–4C-alkylcarbamoyl or -thiocarbamoyl group, an N-1–4C-alkyl-N'-cyanoamidino group, a 1-N-1–4C-alkylamino-2-nitroethylene group, an N-2-propynyl-N'-cyanoamidino group, an aminosulfonylamidino group, the group —N(R10)R11,

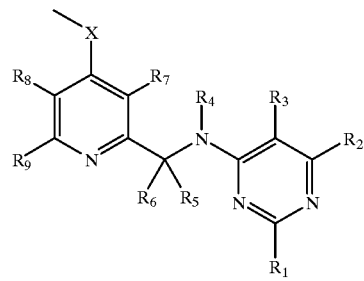

or a cyclic system or bicyclic system which is unsubstituted or substituted by R12 and R13 and which is selected from the group consisting of benzene, naphthalene, furan, thiophene, pyrrole, oxazole, oxazoline, isoxazole, thiazole, thiazoline, isothiazole, imidazole, imidazoline, pyrazole, triazole, tetrazole, thiadiazole, thiodiazole 1-oxide, oxadiazole, pyridine, pyridine N-oxide, pyrimidine, halopyrimidine, piperidine, triazine, pyridone, benzimidazole, imidazopyridine, benzothiazole, benzoxazole, quinoline and imidazopyridazine, in which R10 is 1–7C-alkyl, 3–7C-cycloalkyl or Ar-1–4C-alkyl and R11 is 1–7C-alkyl, 3–7C-cycloalkyl or Ar-1–4C-alkyl, where Ar is phenyl, furyl, naphthyl, tetrahydronaphthyl or phenyl which is substituted by R14, R15 and R16, or in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, thiomorpholine, indoline, 1,2,3,4-tetrahydroquinoline and 1,2,3,4-tetrahydroisoquinoline, where a substituted pyrrolidino group is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl, a substituted piperidino group is substituted by one, two or three identical or different substituents selected from the group consisting of 1–4C-alkyl, 1–4C-alkoxycarbonyl, hydroxy-1–4C-alkyl, phenyl or phenyl-1–4C-alkyl, which is substituted by R14, R15 and R16, benzoyl, benzoyl substituted by halogen and carboxyl, a substituted piperazino group can be substituted in the 2-, 3-, 5- or 6-position by a 1–4C-alkyl group, and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl and carbamoyl, a substituted morpholino group is substituted by one or two identical or different 1–4C-alkyl groups, a substituted thiomorpholino group is substituted by one or two identical or different 1–4C-alkyl groups or a carboxyl group, a substituted indolin-1-yl group can be substituted in the 2- and/or 3-position by a carboxyl group or by one or two identical or different 1–4C-alkyl groups, and can be substituted in the benzo moiety by one or two identical or different substituents selected from the group consisting of 1–4C-alkyl, halogen and nitro, a substituted 1,2,3,1-tetrahydroquinoline group is substituted by one or two identical or different substituents selected from the group consisting of 1–4C-alkyl, 1–4C-alkoxycarbonyl and halogen, a substituted 1,2,3,4-tetrahydroisoquinoline group is substituted by one or two identical or different substituents selected from the group consisting of 1–4C-alkyl, carboxyl and phenyl, R12 is hydrogen, 1–4C-alkyl, hydroxyl, 1–4C-alkoxy, halogen, nitro, guanidino, carboxyl, 1–4C-alkoxycarbonyl, 1–4C-alkyl substituted by R17, phenyl substituted by R14, R15 and R16 or —N(R18)R19, R13 is hydrogen, 1–4C-alkyl, hydroxyl, 1–4C-alkoxy, halogen or trifluoromethyl, R14 is hydrogen, 1–4C-alkyl, hydroxyl, 1–4C-alkoxy, 1–4C-alkylcarbonyl, halogen, trifluoromethyl, 1–4C-alkylamino or nitro, R15 is hydrogen, 1–4C-alkyl, hydroxyl, 1–4C-alkoxy, halogen or nitro, and R16 is hydrogen or trifluoromethyl, R17 is hydroxyl, 1–4C-alkoxy, carboxyl, 1–4C-alkoxycarbonyl or —N (R18) R19, where R18 is hydrogen, 1–4C-alkyl or —CO—R20 and R19 is hydrogen or 1–4C-alkyl, or where R18 and R19, together and including the nitrogen atom to which both are bonded, are a piperidino or morpholino group, R20 is hydrogen, 1–4C-alkyl or 1–4C-alkoxy, X is O (oxygen), N-1–4C-alkyl, NH or S.

Y is O (oxygen), N-1-4C-alkyl, NH, S, 1,4-piperazinylene or 1,4-piperidinylene,

Z is O (oxygen), N-1–4C-alkyl, NH or S or CO, m is a number from 1 to 7, n is a number from 0 to 4, t is the number 0 or 1 and u is the number 0 or 1, or its salts.

3. A compound of the formula I as claimed in claim 1, in which

R1 is hydrogen or 1–4C-alkyl,

R2 is hydrogen or 1–4C-alkyl,

R3 is halogen,

R4 is hydrogen,

R5 is hydrogen,

R6 is hydrogen,

R7 is 1–4C-alkyl or halogen,

R8 is hydrogen,

R9 is hydrogen,

A is 1–7C-alkylene,

G is hydrogen, hydroxyl, 1–4C-alkyl which is completely or mainly substituted by fluorine, the group —N(R10)R11, the glucopyranoside group or a cyclic system which is unsubstituted or substituted by R12 and R13 and which is selected from the group consisting of benzene, furan, thiophene, oxazole, oxazoline, oxazolidinone, thiazole, imidazole, triazole, tetrazole, pyridine, pyrimidine, chloropyrimidine, piperidine, and imidazopyridazine, in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, 1,2,3,4-tetrahydroquinoline and 1,2,3,4-tetrahydroisoquinoline, where a substituted piperazino group is substituted in the 4-position by a substituent selected from the group consisting of 1–4C-alkyl and carbamoyl, R12 is hydrogen, 1–4C-alkyl, hydroxyl, halogen, nitro, carboxyl, phenyl which is substituted by R14, R15 and R16, 1–4C-alkyl which is substituted by R17 or 1–4C-alkoxycarbonyl, R13 is hydrogen or 1–4C-alkyl, R14 is hydrogen, 1–4-alkyl, hydroxyl or 1–4C-alkoxy, R15 ia hydrogen and R16 is hydrogen, R17 is pyridinyl, X is O (oxygen), N-1–4C-alkyl or S, Y is O (oxygen), S or 1,4-piperazinylene, Z is O (oxygen), NH or 5, m is a number from 1 to 4, n is a number from 0 to 2, t is the number 0, 1 or 2 and u is the number 0 or 1, or its salts.

4. A compound of the formula I as claimed in claim 1, in which

R1 is hydrogen or 1–4C-alkyl,

R2 is hydrogen or 1–4C-alkyl,

R3 is chlorine,

R4 is hydrogen,

R5 is hydrogen,

R6 is hydrogen,

R7 is 1–4C-alkyl or chlorine,

R8 is hydrogen,

R9 is hydrogen,

A is 1–4C-alkylene,

G is hydrogen, 1–4C-alkyl which is completely or mainly substituted by fluorine, the group —N(R10)R11 or a cyclic system which is unsubstituted or substituted by R12 and R13 and which is selected from the group consisting of furan, thiophene, oxazoline, oxazolidinone, imidazole, pyridine, pyrimidine, chloropyrimidine and piperidine, in which R10 and R11, together and including the nitrogen atom to which both are bonded, are a piperazine or 1,2,3,4-tetrahydroisoquinoline group, R12 is hydrogen, 1–4C-alkyl, nitro, phenyl which is substituted by R14, R15 and R16 or 1–4C-allyl which is substituted by R17

R13 is hydrogen or 1–4C-alkyl,

R14 is hydrogen or 1–4C-alkoxy,

R15 is hydrogen and

R16 is hydrogen,

R17 is pyridinyl,

X is O (oxygen), N-1–4C-alkyl or S,

Y is O (oxygen), S, or 1,4-piperazinylene,

Z is O (oxygen), NH or S, m is a number from 1 to 4, n is a number from 0 to 2, t is the number 0 or 1 and u is the number 0 or 1, or its salts.

5. A compound of the formula I as claimed in claim 1, in which A is 2–7C-alkylene, X is S and Y is S, t is the number 1 and u is the number 0.

6. A compound of the formula I as claimed in claim 1, in which A is 2–7C-alkylene, X is S and Y is 1,4-piperazinylene, t is the number 1 and u is the number 0.

7. A compound of the formula I as claimed in claim 1, in which A is 2–7C-alkylene, X is O (oxygen) and Y is S, t is the number 1 and u is the number 0.

8. A compound of the formula I as claimed in claim 1, which is selected from the group consisting of (5-Chloro-2,6-dimethyl-pyrimidin-4-yl)-{3-methyl-4-[2-(pyridin-4-ylmethylsulfanyl)-ethoxy]-pyridin-2-ylmethyl}-amine, (5-Chloro-2,6-dimethyl-pyrimidin-4-yl)-(3-methyl-4-{2-[2-(2-methyl-5-nitro-imidazol-1-yl)-ethylsulfanyl]-ethoxy}-pyridin-2-ylmethyl)-amine, (5-Chloro-2,6-dimethyl-pyrimidin-4-yl)-(3-methyl-4-{3-[2-(2-methyl-5-nitro-imidazol-1-yl)-ethylsulfanyl]-propoxy}-pyridin-2-ylmethyl)-amine, (5-Chloro-2,6-dimethyl-pyrimidin-4-yl)-(3-methyl-4-(2-[2-(pyridin-4-ylmethylsulfanyl)-ethoxy]-ethylsulfanyl}pyridin-2-ylmethyl)-amine, (5-Chloro-2,6-dimethyl-pyrimidin-4-yl)-{3-methyl-4-[3-(pyridin-2-yl-methylsulfanyl)-propylsulfanyl]-pyridin-2-ylmethyl}-amine and (5-Chloro-pyrimidin-4-yl)-(3-methyl-4-}2-[2-(2-methyl-5-nitro-imidazol-1-yl)-ethylsulfanyl]-ethoxy}-pyridin-2-ylmethyl)-amine or its salts.

9. A pharmaceutical composition comprising a compound of the formula I as claimed in claim 1 and/or its pharmacologically tolerable salts together with a pharmaceutically acceptable carrier.

10. A method for controlling Helicobacter bacteria comprising administering compounds of the formula I as claimed in claim 1 or their pharmacologically tolerable salts to an animal in need thereof.

\* \* \* \* \*

UNITED STATES PATENT AND TRADEMARK OFFICE
CERTIFICATE OF CORRECTION

PATENT NO. : 6,395,732 B1
DATED : May 28, 2002
INVENTOR(S) : Peter Zimmermann and Gerhard Grundler It is certified that error appears in the above-identified patent and that said Letters Patent is hereby corrected as shown below:

Column 51,
Line 37, after "1-4C-alkyl or" please replace "1-4-alkoxy," with -- 1-4C-alkoxy, --.

Column 53,
Line 6, after "a substituted" and before "group is", please replace "1,2,3,1-tetrahydroquinoline" with -- 1,2,3,4-tetrahydroquinoline --.
Line 38, after "NH or S" please replace "." with -- , --.

Column 54,
Line 21, after "is hydrogen", and before "hydroxyl or", please replace "1-4-alkyl," with -- 1-4C-alkyl, --.
Line 22, after "R15" and before "hydrogen", please replace "ia" with -- is --.
Line 28, after "NH or", please replace "5", with -- S, --.

Column 56,
Line 7, after "(3-methyl-4-" and before "2-[2-(pyridin", please replace "(" with -- { --.
Line 11, after "(3-methyl-4-" and before "2-[2-(2-", please replace "}" with -- { --.

Signed and Sealed this

First Day of October, 2002

Attest:

*Attesting Officer*

JAMES E. ROGAN
*Director of the United States Patent and Trademark Office*